US008518651B2

(12) United States Patent
Sato et al.

(10) Patent No.: US 8,518,651 B2
(45) Date of Patent: Aug. 27, 2013

(54) MARKER FOR IDENTIFICATION OF TISSUE TYPE OF EPITHELIAL OVARIAN CANCER, AND METHOD FOR DETERMINATION OF THE OCCURRENCE OF EPITHELIAL OVARIAN CANCER BASED ON TISSUE TYPE BY USING THE MARKER

(75) Inventors: Taka-aki Sato, Kyoto (JP); Atsuhiko Toyama, Kyoto (JP); Takashi Shimada, Kyoto (JP); Tetsuyoshi Sugita, Kyoto (JP); Daisuke Aoki, Tokyo (JP); Atsushi Suzuki, Tokyo (JP); Nobuyuki Susumu, Tokyo (JP); Hiroyuki Nomura, Tokyo (JP)

(73) Assignees: Shimadzu Corporation, Kyoto (JP); Keio University, Tokyo (JP)

( * ) Notice: Subject to any disclaimer, the term of this patent is extended or adjusted under 35 U.S.C. 154(b) by 6 days.

(21) Appl. No.: 12/527,191

(22) PCT Filed: Feb. 15, 2008

(86) PCT No.: PCT/JP2008/053006
§ 371 (c)(1),
(2), (4) Date: Aug. 13, 2009

(87) PCT Pub. No.: WO2008/099972
PCT Pub. Date: Aug. 21, 2008

(65) Prior Publication Data
US 2010/0075354 A1 Mar. 25, 2010

(30) Foreign Application Priority Data

Feb. 16, 2007 (JP) ................................. 2007-036556
Oct. 2, 2007 (JP) ................................. 2007-259281

(51) Int. Cl.
*G01N 33/53* (2006.01)
(52) U.S. Cl.
USPC ........................................................ 435/7.1
(58) Field of Classification Search
None
See application file for complete search history.

(56) References Cited

FOREIGN PATENT DOCUMENTS

| JP | 2006-512586 A | 4/2006 |
| JP | 2006-284389 A | 10/2006 |
| JP | 2006-308533 A | 11/2006 |
| WO | WO-2004/013609 A2 | 2/2004 |

OTHER PUBLICATIONS

Hee Jung An et al (Journal of Proteome Research, 2006, 5(5):1082-1090).*
Zou et al (Nutr J, 2005, 4(25): 1-12).*
Zhu et al (Proteomics, 2006, 6: 5846-5856).*
Zhu et al (Proteomics, 2006, 6: 5846-5858).*
Tockman et al (Cancer Res., 1992, 52:2711s-2718s).*
Zimmerman et al (Cancer Letters, 2004, 209: 111-118).*
Zhu et al (Proteomics, 2006, 6(21): 5846-5856).*
Schwartz (Cancer Research, 2002, 62: 4722-4729).*
Balzer et al (Modern Pathology 92nd Annual Meeting of the United States and Canadian Academy of Pathology, 2003, 16(1): pp. 181A).*
International Preliminary Report on Patentability for the Application No. PCT/JP2008/053006 mailed Aug. 27, 2009.
International Search Report for the Application No. PCT/JP2008/053006 mailed Mar. 25, 2008.
Okamoto, Satoshi et al., "Ber-EP4 and Anti-Calretinin Antibodies: A Useful Combination for Differential Diagnosis of Various Histological Types of Ovarian Cancer Cells and Mesothelial Cells", Tohoku J. Exp. Med., 2005, vol. 206, No. 1, pp. 31-40.
Suwa, Shinobu et al., "Ransogan wa Men'eki Soshiki ga kakuteki ni Abunrui Dekiru" ("Ovarian Cancer Can Be Subclassified Immunohistochemically"), Yamagata Journal of Medicine, 2005, vol. 39, No. 2, pp. 128-130.
Suzuki, Atsushi et al., "Ransogan no Kaku Soshikigata Tokuiteki Biomarker ni Motozuku Shindanyo Microarray DNA Chip Sakusei" ("Fabrication of Diagnostic Microarray DNA Chip Based on Each Specific Histological Type of Ovarian Cancer Biomarker"), Nippon Sanfujinka Gakkai Zasshi (Journal of Japan Society of Obstetrics and Gynecology), Feb. 2007 Hakko, vol. 59, No. 2, p. 409 (P1-181).
Liu, Huiqing et al,, "A Comparative Study on Feature Selection and Classification Methods Using Gene Expression Profiles and Proteomic Patterns", Genome Informatics, 2002, vol. 13, pp. 51-60.
Alaiya, Ayodele et al., "Classification of Human Ovarian Tumors Using Multivariate Data Analysis of Polypeptide Expression Patterns", Int. J. Cancer, 2000, vol. 86, No. 5, pp. 731-736.
Morita, Atsushi "Keiko Difference Gel Nijigen Denki Eido ni yoru Ransogan Shindan Marker Kensaku" ("Search for Diagnostic Ovarian Cancer Markers with Fluorescent Two-Dimensional Difference Gel Electrophoresis (2D-DIGE)"), Journal of Electrophoresis, 2006, vol. 50, No. 3, pp. 179-185.
Izumi, Shunsuke et al., "Biomedical Bunya ni Okeru Shitsuryo Bunsekiho no Saikin no Tenkai" ("Recent Development of Mass Spectrometry in the Field of Biomedical"), Pharmacia, 2005, vol. 41, No. 11, pp. 1047-1052.
MacDonald, N.D. et al., "Is There a Place for Screening in Ovarian Cancer?", European Journal of Obstetrics & Gynecology and Reproductive Biology, 1999, vol. 82, pp. 155-157.

(Continued)

*Primary Examiner* — Sean Aeder
(74) *Attorney, Agent, or Firm* — Cheng Law Group, PLLC

(57) ABSTRACT

It is provided a method for identification of the morbidity of epithelial ovarian cancer based on a tissue-type in view of molecular typing which is different from a conventional histopathology, and a marker for identification of a tissue-type of epithelial ovarian cancer. A method for identification of the morbidity of epithelial ovarian cancer based on a tissue-type, comprising: subjecting a sample originated from an individual of interest to a treatment for detecting at least one selected from the group consisting of biological molecules specifically showing an upregulation in expression in a specific tissue-type of epithelial ovarian cancer, and/or at least one selected from the group consisting of biological molecules specifically showing a downregulation in expression in a specific tissue-type of epithelial ovarian cancer, and identifying whether or not the significant detection of the protein is achieved, thereby identifying the tissue-type.

1 Claim, 14 Drawing Sheets

(56) References Cited

OTHER PUBLICATIONS

Zhang, Zhen et al., "Three Biomarkers Identified from Serum Proteomic Analysis for the Detection of Early Stage Ovarian Cancer", Cancer Research, Aug. 2004, vol. 64, pp. 5882-5890.

Check, Erika "Proteomics and Cancer: Running Before we can Walk?", Nature, Jun. 2004, vol. 249, pp. 496-497.

An, Hee Jung et al., "Comparative Proteomics of Ovarian Epithelial Tumors", Journal of proteome research, 2006, vol. 5, No. 5, pp. 1082-1090.

Okamoto, Satoshi et al., "Ber-EP4 and Anti-Calretinin Antibodies: A Useful Combination for Differential Diagnosis of Various Histological Types of Ovarian Cancer Cells and Mesothelial Cells", Tohoku J. Exp. Med., 2005, vol. 206, pp. 31-40.

* cited by examiner

Fig. 14

Classification based on expression levels of four proteins

| Classification Category | Combination of Expression Level (+/−) | | | | Classification Result in Actual Specimen | | | |
|---|---|---|---|---|---|---|---|---|
| | ANXA4 | MASPIN | CRABP2 | PSAT1 | Clear cell (n=13) | Endometrioid (n=11) | Serous (n=11) | Mucinous (n=5) |
| Clear cell | + | − | − | + | 13 | 0 | 0 | 0 |
| Mucinous | + | + | − | − | 0 | 0 | 0 | 5 |
| Serous | − | + | + | − | 0 | 0 | 1 | 0 |
| | − | − | + | − | 0 | 2 | 7 | 0 |
| | − | − | + | + | 0 | 0 | 3 | 0 |
| Endometrioid | − | − | − | + | 0 | 5 | 0 | 0 |
| | − | − | − | − | 0 | 3 | 0 | 0 |
| | + | − | − | − | 0 | 1 | 0 | 0 |

MARKER FOR IDENTIFICATION OF TISSUE TYPE OF EPITHELIAL OVARIAN CANCER, AND METHOD FOR DETERMINATION OF THE OCCURRENCE OF EPITHELIAL OVARIAN CANCER BASED ON TISSUE TYPE BY USING THE MARKER

TECHNICAL FIELD

The present invention relates to techniques of screening, diagnosis, examination, follow up, and classification of epithelial ovarian cancer (EOC). More specifically, the present invention relates to molecular typing of a tissue-type of epithelial ovarian cancer. In other words, the present invention relates to a marker for identification of a tissue-type of epithelial ovarian cancer and a method for identification of epithelial ovarian cancer based on a tissue-type using the same.

BACKGROUND ART

Ovarian cancer is a case whose number is the second highest in malignant tumors of female genitalia, and has the highest lethality. This mostly occurs in premenopausal or postmenopausal women. Only in the U.S., annually 26,000 people are newly diagnosed to suffer from ovarian cancer, and 16,000 patients are deceased (in 2004). Five year survival rates for classified stages are 90% for stage I, 70% for stage II, 25% for stage III, and 10% for stage IV, and prognosis of stage III or later is very bad. Therefore, early diagnosis would be the most important issue for improving the long term survival rate. However, most of ovarian cancers in early stage are silent, and a noninvasive definitive diagnosis method has not been established. From these facts, there is rarely the case that ovarian cancer is diagnosed in early stage and completely cured. Therefore, there is a strong need for a tumor marker available for early diagnosis.

The term "tumor marker" refers to a biological molecule (concretely a protein) that is specifically produced by a tumor, and is generally used in the concept of diagnosing presence or absence of a tumor by detection or quantification in bodily fluids (mainly in blood).

As an ovarian cancer marker that is widely used at present in clinical practice, CA125 can be recited first. This marker shows a high positive rate in a malignant tumor, and has been actually used for several tens of years. On the contrary, however, the marker shows a low positive rate and too poor specificity in early stage ovarian cancer. Therefore, it has a drawback that it can not be used in early diagnosis. This is described in MacDonald et al., 1999.

Later, Zhang et al. proposed a method of early diagnosis of ovarian cancer by identifying three kinds of tumor markers from serum of patients suffering from ovarian cancer using a technique called SELDI-TOF-MS combining a surface processing technique and mass spectrometry, and diagnosing the cancer based on the combination of these tumor markers and CA125 (Zhang et al., 2004) (Open Patent Publication No. 2006-512586). However, as described in Nature, 2004, there is an opinion that the methodology lacks a scientific basis. For this reason, this method has not been brought into practical use yet.

On the other hand, Hee Jung An et al., 2006 describes development of a tumor marker taking the difference between tissue-types of epithelial ovarian cancer into account.

Patent Document 1: Open Patent Publication No. 2006-512586
Non Patent Document 1: MacDonald N D, Jacobs I J. Is there a place for screening in ovarian cancer? European journal of obstetrics, gynecology, and reproductive biology 1999; 82(2): 155-7.
Non Patent Document 2: Zhang Z, Bast R C, Jr., Yu Y, et al. Three biomarkers identified from serum proteomic analysis for the detection of early stage ovarian cancer. Cancer research 2004; 64(16):5882-90.
Non Patent Document 3: Check E. Proteomics and cancer: running before we can walk? Nature 2004; 429(6991):496-7.
Non Patent Document 4: An H J, Kim D S, Park Y K, et al. Comparative proteomics of ovarian epithelial tumors. Journal of proteome research 2006; 5(5):1082-90.

DISCLOSURE OF THE INVENTION

Object of the Invention

Collectively called "ovarian tumor" is finely classified histopathologically depending on the form, site of development and so on, and has more than thirty kinds including benignant ones. In conventional tumor marker screening of ovarian cancer, the tissue-type of epithelial ovarian cancer is not particularly taken into account. However, resistance to an anticancer agent and sensitivity to CA-125, as well as metastatic phenotype actually differ depending on the tissue-type. Therefore, a tissue-type will largely influence on selection of the treatment method.

In very recent years, as described in the above Hee Jung An et al., 2006, development of a tumor marker taking the difference between tissue-types into account is also reported. However, development of such a tumor marker is based on a comparative analysis between a normal tissue and a cancer tissue of a specific molecule. In biomarker screening based on comparison of components contained in a biological sample from a healthy person and components in a biological sample from a cancer patient, however, lack of the causal logic and low reproducibility are often seen as problematic points.

On the other hand, a comprehensive comparative analysis between different tissue-types of a specific molecule is not known at present. Therefore, it can be said that existence of a molecule that enables noninvasive tissue-type diagnosis has not been disclosed yet.

At present, there is no other established method for classification of the tissue-type of ovarian tumor than the method conducted based on histopathology after extirpation. Also physicians who are constantly able to make an appropriate diagnosis are limited. These would be major reasons for hung-up of research using clinical specimens in Japan. Therefore, a tumor marker that enables tissue-type diagnosis in molecular level has large significance in various aspects, and high demand is prospected especially in clinical practice.

It is an object of the present invention to provide a method for identification of the morbidity of epithelial ovarian cancer based on a tissue-type in view of molecular typing which is different from a conventional histopathology. In other words, it is an object of the present invention to provide a marker for identification of a tissue-type of epithelial ovarian cancer.

SUMMARY OF THE INVENTION

Inventors of the present application found a new point of view, namely, biomarker screening starting from determination of the tissue-type. Inventors of the present application made profiling of epithelial ovarian cancer based on the new point of view of examining variation in expression between tissue-types using an epithelial ovarian cancer clinical tissue specimen for which correct tissue-type diagnosis has been made from the viewpoint of histopathology.

Here, profiling of epithelial ovarian cancer in the present invention refers to clarifying group of biological molecules that are expressed specifically in high level or in low level in a specific tissue-type of epithelial ovarian cancer. Concretely, an expression amount of a biological molecule expressed in a biological sample suffering from epithelial ovarian cancer is examined for each tissue-type, and group of biological molecules whose expression varies relatively between tissue-types are comprehensively analyzed.

The present inventors identified and quantified all expressed proteins from epithelial ovarian cancer clinical tissue specimens of different tissue-types, and comprehensively analyzed group of proteins whose expression relatively varies between tissue-types. Then, the inventors revealed existence of a series of proteins that significantly show an upregulation/downregulation in expression in a specific tissue-type. The revealed series of proteins were classified according to the difference in nature, namely, in which tissue-type the specific upregulation/downregulation in expression was shown.

Particularly notable is that diverse proteins were found respectively in clear cell cancer, endometrioid carcinoma, serous adenocarcinoma and mucinous adenocarcinoma of epithelial ovarian cancer, namely proteins having such an expression pattern that expression is significant only in a specific one kind of tissue-type were found. This supports the concept that the epithelial ovarian cancer is clearly a diverse cancer in respective tissue-types. And since such a protein can by itself be a tumor marker for early diagnosis concerning epithelial ovarian cancer of a specific tissue-type, it was found that tissue-types can be identified using such proteins.

Also a protein having such an expression pattern that expression occurs specifically significantly in two kinds of tissue-types among clear cell cancer, endometrioid carcinoma, serous adenocarcinoma and mucinous adenocarcinoma of epithelial ovarian cancer, and a protein having such an expression pattern that the expression is downregulated in a specific one kind of tissue-type were found.

Therefore, it was also found that more accurate identification of a tissue-type can be realized by using not only the above tumor marker singly, but also using an appropriate combination of the protein that is specifically significantly expressed in two kinds of tissue-types and the protein whose expression is downregulated in a specific one kind of tissue-type as markers for identification of a tissue-type.

As described above, from the overview of the data revealed by profiling made by the present inventors, the concept was established that epithelial ovarian cancer is clearly a diverse cancer in respective tissue-types in molecular level, as one disease concept of epithelial ovarian cancer. This led to development of a tissue-type classification system of epithelial ovarian cancer, and as a result, the present inventors accomplished a method for identification of the morbidity of epithelial ovarian cancer based on a tissue-type.

The present invention includes the following inventive aspects.

The following (1) to (15) are methods for identification of the morbidity of epithelial ovarian cancer based on a tissue-type. The method of the present invention involves determining a tissue-type by examining an expression amount of a biological molecule that shows a specific expression tendency in a specific tissue-type of epithelial ovarian cancer, used as a marker for identification of a tissue-type.

(1)
A method for identification of the morbidity of epithelial ovarian cancer based on a tissue-type, comprising:
subjecting a sample originated from an individual of interest to a treatment for detecting
at least one selected from the group consisting of biological molecules specifically showing an upregulation in expression in a specific tissue-type of epithelial ovarian cancer, and/or
at least one selected from the group consisting of biological molecules specifically showing a downregulation in expression in a specific tissue-type of epithelial ovarian cancer, and
identifying whether or not the significant detection of the protein is achieved, thereby identifying the tissue-type.

The term "morbidity" widely refers to pathologic conditions, and the expression "identification of the morbidity of a cancer" is used in the meanings including detection (screening), diagnosis, monitoring, staging and prognostication of a cancer.

The term "specific tissue-type" means one or plural tissue-type(s). Therefore, a "molecules specifically showing an upregulation/downregulation in expression in a specific tissue-type" means that it is at least not a housekeeping molecule, and is preferably a molecule specifically showing an upregulation/downregulation in expression in one or two tissue-type(s). In the method of the present invention, it is possible to identify the tissue-type from clear cell type (hereinafter, Clear Cell), endometrioid carcinoma type (hereinafter, Endometrioid), serous adenocarcinoma type (hereinafter, Serous), and mucinous adenocarcinoma type (hereinafter, Mucinous) in epithelial ovarian cancer. In this case, the "specific tissue-type" refers to specific one or two tissue-type(s) in these four types.

The following (2) describes profiling for finding a biological molecule showing a specific expression tendency (concretely, an upregulation in expression or a downregulation in expression) for a specific tissue-type, namely, a marker for identification of a tissue-type.

(2)
The method for identification of the morbidity of epithelial ovarian cancer based on a tissue-type according to (1), wherein the group consisting of the biological molecules specifically showing an upregulation in expression in a specific tissue-type of epithelial ovarian cancer, and the group consisting of the biological molecules specifically showing a downregulation in expression in a specific tissue-type of epithelial ovarian cancer are found by profiling that includes
preparing samples originated from patients of epithelial ovarian cancer for plural tissue-types whose tissue-types are definitively diagnosed,
quantifying biological molecules expressed in the samples for each of the plural tissue-types, and
screening biological molecules whose quantified value in a specific tissue-type upregulates or downregulates by a significant variation amount relative to quantified values in other tissue-types, from biological molecules expressed in the samples.

In the following (3), expression amounts are examined for a plurality of biological molecules showing a specific expression tendency for a specific tissue-type, and a tissue-type is identified by combination of measurement results of expression amounts. More specifically, by combination of a plurality of identification markers, the morbidity of epithelial ovarian cancer based on a tissue-type is identified.

Further, the following (3) and (4) to (15) are directed to the cases where biological molecules are proteins. In the present invention, a protein includes a peptide having a relatively small molecular weight (for example, a peptide forming a part of proteins described in the following (4) to (15)). As a substance other than a protein, substances that are generated by an action of a protein (for example, metabolites such as sugar, lipid and the like) and so on may be recited. The method based on the combination of a plurality of identification markers in the following (3) may be practiced in the same way in a biological molecule other than a protein.

(3)

The method for identification of the morbidity of epithelial ovarian cancer based on a tissue-type according to (1) or (2), wherein the group consisting of the biological molecules specifically showing an upregulation in expression in a specific tissue-type of epithelial ovarian cancer includes protein C(+) specifically showing an upregulation in expression only in Clear Cell type, protein E(+) specifically showing an upregulation in expression only in Endometrioid Carcinoma type, protein S(+) specifically showing an upregulation in expression only in Serous Adenocarcinoma type, protein M(+) specifically showing an upregulation in expression only in Mucinous Adenocarcinoma type; protein CS(+) specifically showing an upregulation in expression in Clear Cell type and in Serous Adenocarcinoma type, protein CM(+) specifically showing an upregulation in expression in Clear Cell type and in Mucinous Adenocarcinoma type, protein ES(+) specifically showing an upregulation in expression in Endometrioid Carcinoma type and in Serous Adenocarcinoma type, protein SM(+) specifically showing an upregulation in expression in Serous Adenocarcinoma type and in Mucinous Adenocarcinoma type, protein CE(+) specifically showing an upregulation in expression in Clear Cell type and in Endometrioid Carcinoma type, and protein EM(+) specifically showing an upregulation in expression in Endometrioid Carcinoma type and in Mucinous Adenocarcinoma type, the group consisting of the biological molecules specifically showing a downregulation in expression in a specific tissue-type of epithelial ovarian cancer includes protein M(−) showing a downregulation in expression only in Mucinous Adenocarcinoma type, protein S(−) showing a downregulation in expression only in Serous Adenocarcinoma type, protein E(−) showing a downregulation in expression only in Endometrioid Carcinoma type, and protein C(−) showing a downregulation in expression only in Clear Cell type, and detection results for a plurality of proteins arbitrarily selected from the proteins C(+), E(+), S(+), M(+), CS(+), CM(+), ES(+), SM(+), CE(+), EM(+), M(−), S(−), E(−), and C(−) are combined.

In the following (4) to (15), as the biological molecule showing a specific expression tendency for a specific tissue-type, a protein found by profiling devised by the present inventors is used.

(4)

The method for identification of the morbidity of epithelial ovarian cancer based on a tissue-type according to (3), wherein the protein C(+) specifically showing an upregulation in expression only in Clear Cell type is selected from the group consisting of Acid ceramidase precursor,
Alpha crystallin B chain,
Annexin A1 (Annexin-1),
Annexin A4 (Annexin-4),
Carbonic anhydrase 1,
Catechol O-methyltransferase,
Cellular retinoic acid-binding protein 1,
Cystathionine gamma-lyase,
Endoplasmic reticulum protein ERp29 precursor,
Ferritin heavy chain,
Glutathione peroxidase 3 precursor,
Guanine deaminase,
Laminin subunit beta-1 precursor (Laminin B1 chain),
Laminin subunit gamma-1 precursor (Laminin B2 chain),
L-lactate dehydrogenase B chain,
Low molecular weight phosphotyrosine protein phosphatase,
Methylcrotonoyl-CoA carboxylase beta chain, mitochondrial precursor,
Nicotinamide N-methyltransferase,
Peroxiredoxin-2,
Peroxiredoxin-6,
Phosphomannomutase 2,
Phosphoserine aminotransferase,
Protein SET,
Purine nucleoside phosphorylase,
Pyridoxal kinase,
Serum amyloid P-component precursor,
SPRY domain-containing protein 4,
Superoxide dismutase [Mn], mitochondrial precursor,
Synaptic vesicle membrane protein VAT-1 homolog,
Thioredoxin domain-containing protein 12 precursor,
Transaldolase,
Triosephosphate isomerase,
Tryptophanyl-tRNA synthetase, cytoplasmic, and
Uncharacterized protein C7orf24.

In the above (4), at least Annexin A4 (Annexin-4) is selected when a marker molecule quantification method allowing distinction between presence and absence of post-translational modification of a protein is used in the above treatment for detecting.

(5)

The method for identification of the morbidity of epithelial ovarian cancer based on a tissue-type according to (3) or (4), wherein the protein E(+) specifically showing an upregulation in expression only in Endometrioid Carcinoma type is selected from the group consisting of ASRGL1 protein, and
Parvalbumin alpha.

(6)

The method for identification of the morbidity of epithelial ovarian cancer based on a tissue-type according to any of (3) to (5), wherein the protein S(+) specifically showing an upregulation in expression only in Serous Adenocarcinoma type is selected from the group consisting of Astrocytic phosphoprotein PEA-15,
c-Myc-responsive protein Rcl,
Cyclin-dependent kinase inhibitor 2A,
F-actin capping protein subunit alpha-1,
Gamma-synuclein (Breast cancer-specific gene 1 protein),
Glyoxalase domain-containing protein 4,
Ras-related protein Rab-2A,
Replication protein A 32 kDa subunit,
S100 calcium-binding protein A13,
Small ubiquitin-related modifier 2 precursor (SUMO-2), and
Ubiquinol-cytochrome c reductase complex 11 kDa protein, mitochondrial precursor.

(7)

The method for identification of the morbidity of epithelial ovarian cancer based on a tissue-type according to any of (3) to (6), wherein the protein M(+) specifically showing an upregulation in expression only in Mucinous Adenocarcinoma type is selected from the group consisting of Fatty acid-binding protein, liver,
Serpin B5 precursor (Maspin), Thioredoxin (ATL-derived factor), and
Transgelin-2.

(8)

The method for identification of the morbidity of epithelial ovarian cancer based on a tissue-type according to any of (3) to (7), wherein the protein CS(+) specifically showing an upregulation in expression only in Clear Cell type and in Serous Adenocarcinoma type is selected from the group consisting of 6-phosphogluconolactonase, and
Ubiquinol-cytochrome-c reductase complex core protein I, mitochondrial precursor.

(9)

The method for identification of the morbidity of epithelial ovarian cancer based on a tissue-type according to any of (3) to (8), wherein the protein CM(+) specifically showing an upregulation in expression in Clear Cell type and in Mucinous Adenocarcinoma type is selected from the group consisting of Carbonic anhydrase 2,
Delta(3,5)-Delta(2,4)-dienoyl-CoA isomerase,
Thiosulfate sulfurtransferase, and
Annexin A4 (Annexin-4).

In the above (9), Annexin A4 (Annexin-4) is selected when a marker molecule quantification method not allowing distinction between presence and absence of post-translational modification of a protein is used in the above treatment for detecting.

(10)

The method for identification of the morbidity of epithelial ovarian cancer based on a tissue-type according to any of (3) to (9), wherein the protein ES(+) specifically showing an upregulation in expression in Endometrioid Carcinoma type and in Serous Adenocarcinoma type is selected from the group consisting of Rho GDP-dissociation inhibitor 2, and
Transgelin.

(11)

The method for identification of the morbidity of epithelial ovarian cancer based on a tissue-type according to any of (3) to (10), wherein the protein SM(+) specifically showing an upregulation in expression in Serous Adenocarcinoma type and in Mucinous Adenocarcinoma type is selected from the group consisting of Barrier-to-autointegration factor,
Cellular retinoic acid-binding protein 2,
S100 calcium-binding protein A11,
S100 calcium-binding protein A4,
S100 calcium-binding protein A6,
Selenium-binding protein 1, and
Transgelin-2.

(12)

The method for identification of the morbidity of epithelial ovarian cancer based on a tissue-type according to any of (3) to (11), wherein the protein CE(+) specifically showing an upregulation in expression in Clear Cell type and in Endometrioid Carcinoma type is selected from the group consisting of Calcyphosin, and
Fibrinogen beta chain precursor.

(13)

The method for identification of the morbidity of epithelial ovarian cancer based on a tissue-type according to any of (1) to (12), wherein the protein M(−) showing a downregulation in expression only in Mucinous Adenocarcinoma type is Haloacid dehalogenase-like hydrolase domain-containing protein 2.

(14)

The method for identification of the morbidity of epithelial ovarian cancer based on a tissue-type according to any of (3) to (13), wherein the protein E(−) showing a downregulation in expression only in Endometrioid Carcinoma type is selected from the group consisting of Bis(5'-nucleosyl)-tetraphosphatase [asymmetrical],
Chloride intracellular channel protein 1, and
Monoamine-sulfating phenol sulfotransferase.

(15)

The method for identification of the morbidity of epithelial ovarian cancer based on a tissue-type according to any of (3) to (14), wherein the protein C(−) showing a downregulation in expression only in Clear Cell type is selected from the group consisting of Acyl-CoA-binding protein,
Coactosin-like protein,
SH3 domain-binding glutamic acid-rich-like protein,
Transgelin, and
Uncharacterized protein C6orf115.

The following (16) to (24) relate to markers for identification of a tissue-type of epithelial ovarian cancer.

Among these, as shown in (16) to (19), a protein that is specific for only one tissue-type may be an early diagnosis marker of ovarian cancer of the tissue-type. (16) is a tumor marker of clear cell cancer, (17) is a tumor marker of endometrioid carcinoma, (18) is a tumor marker of serous adenocarcinoma, and (19) is a tumor marker of mucinous adenocarcinoma.

(16)

A marker for identification of a tissue-type of epithelial ovarian cancer, comprising, as protein C(+) specifically showing an upregulation in expression only in Clear Cell type, at least one kind of protein selected from the group consisting of Acid ceramidase precursor,
Alpha crystallin B chain,
Annexin A1 (Annexin-1),
Annexin A4 (Annexin-4),
Carbonic anhydrase 1,
Catechol O-methyltransferase,
Cellular retinoic acid-binding protein 1,
Cystathionine gamma-lyase,
Endoplasmic reticulum protein ERp29 precursor,
Ferritin heavy chain,
Glutathione peroxidase 3 precursor,
Guanine deaminase,
Laminin subunit beta-1 precursor (Laminin B1 chain),
Laminin subunit gamma-1 precursor (Laminin B2 chain),
L-lactate dehydrogenase B chain,
Low molecular weight phosphotyrosine protein phosphatase,
Methylcrotonoyl-CoA carboxylase beta chain, mitochondrial precursor,
Nicotinamide N-methyltransferase,
Peroxiredoxin-2,
Peroxiredoxin-6,
Phosphomannomutase 2,
Phosphoserine aminotransferase,
Protein SET,
Purine nucleoside phosphorylase,
Pyridoxal kinase,
Serum amyloid P-component precursor,
SPRY domain-containing protein 4,
Superoxide dismutase [Mn], mitochondrial precursor,
Synaptic vesicle membrane protein VAT-1 homolog,
Thioredoxin domain-containing protein 12 precursor, Transaldolase,
Triosephosphate isomerase,
Tryptophanyl-tRNA synthetase, cytoplasmic, and
Uncharacterized protein C7orf24.

In the above (16), at least Annexin A4 (Annexin-4) is used when marker molecule quantification is executed using a method allowing distinction between presence and absence of post-translational modification.

(17)

A marker for identification of a tissue-type of epithelial ovarian cancer, comprising, as protein E(+) specifically showing an upreagulation in expression only in Endometrioid Carcinoma type, at least one of protein selected from the group consisting of
ASRGL1 protein, and
Parvalbumin alpha.

(18)

A marker for identification of a tissue-type of epithelial ovarian cancer, comprising, as protein S(+) specifically showing an upregulation in expression only in Serous Adenocarcinoma type, at least one of protein selected from the group consisting of
Astrocytic phosphoprotein PEA-15,
c-Myc-responsive protein Rcl,
Cyclin-dependent kinase inhibitor 2A,
F-actin capping protein subunit alpha-1,
Gamma-synuclein (Breast cancer-specific gene 1 protein),
Glyoxalase domain-containing protein 4,
Ras-related protein Rab-2A,
Replication protein A 32 kDa subunit,
S100 calcium-binding protein A13,
Small ubiquitin-related modifier 2 precursor (SUMO-2), and
Ubiquinol-cytochrome c reductase complex 11 kDa protein, mitochondrial precursor.

(19)

A marker for identification of a tissue-type of epithelial ovarian cancer, comprising, as protein M(+) specifically showing an upregulation in expression only in Mucinous Adenocarcinoma type, at least one of protein selected from the group consisting of
Fatty acid-binding protein, liver,
Serpin B5 precursor (Maspin),
Thioredoxin (ATL-derived factor), and
Transgelin-2.

The following (20) relates to a protein specifically showing significant expression in two tissue-types. A specific one protein selected from (20) is not used solely, but is used in combination with other proteins. Examples of other proteins include proteins described in (20) showing an expression pattern different from that of the above described specific one protein selected, proteins described in the above (16) to (19), and proteins described in the later-described (21) to (24).

(20)

A marker for identification of a tissue-type of epithelial ovarian cancer, comprising at least one of protein selected from the group consisting of:
6-phosphogluconolactonase, and
Ubiquinol-cytochrome-c reductase complex core protein I, mitochondrial precursor
as protein CS(+) specifically showing an upregulation in expression in Clear Cell type and in Serous Adenocarcinoma type;
Carbonic anhydrase 2,
Delta(3,5)-Delta(2,4)-dienoyl-CoA isomerase,
Thiosulfate sulfurtransferase, and
Annexin A4 (Annexin-4)
as protein CM(+) specifically showing an upregulation in expression in Clear Cell type and in Mucinous Adenocarcinoma type;
Rho GDP-dissociation inhibitor 2, and
Transgelin
as protein ES(+) specifically showing an upregulation in expression in Endometrioid Carcinoma type and in Serous Adenocarcinoma type;
Barrier-to-autointegration factor,
Cellular retinoic acid-binding protein 2,
S100 calcium-binding protein A11,
S100 calcium-binding protein A4,
S100 calcium-binding protein A6,
Selenium-binding protein 1, and
Transgelin-2
as protein SM(+) specifically showing an upregulation in expression in Serous Adenocarcinoma type and in Mucinous Adenocarcinoma type; and
Calcyphosin, and
Fibrinogen beta chain precursor
as protein CE(+) specifically showing an upregulation in expression in Clear Cell type and in Endometrioid Carcinoma type.

In the above (20), the marker Annexin A4 (Annexin-4) is used when marker molecule quantification is executed using a method not allowing distinction between presence and absence of post-translational modification.

(21)

A marker for identification of a tissue-type of epithelial ovarian cancer, comprising Haloacid dehalogenase-like hydrolase domain-containing protein 2 as protein M(−) showing a downregulation in expression only in Mucinous Adenocarcinoma type.

(22)

A marker for identification of a tissue-type of epithelial ovarian cancer, comprising at least one protein selected from the group consisting of
Bis(5'-nucleosyl)-tetraphosphatase [asymmetrical],
Chloride intracellular channel protein 1, and
Monoamine-sulfating phenol sulfotransferase
as protein E(−) showing a downregulation in expression only in Endometrioid Carcinoma type.

(23)

A marker for identification of a tissue-type of epithelial ovarian cancer, comprising at least one protein selected from the group consisting of
Acyl-CoA-binding protein,
Coactosin-like protein,
SH3 domain-binding glutamic acid-rich-like protein,
Transgelin, and
Uncharacterized protein C6orf115
as protein C(−) showing a downregulation in expression only in Clear Cell type.

(24)

A kit for identification of a tissue-type of epithelial ovarian cancer, comprising at least two proteins selected from the proteins according to (16) to (23).

The present invention is also directed to a pharmaceutical composition for treatment of a cancer described in the following (25) and (26). The term "treatment of a cancer" includes killing of a cancer cell, and suppressing growth of a cancer cell.

(25)

A pharmaceutical composition for inducing reaction that promotes killing of a cancer cell and/or suppression of growth of a cancer cell by being supplied to a cancer cell, comprising at least one of antibody that immunospecifically binds to the identification marker according to (16) to (19).

(26)

A pharmaceutical composition for promoting immune response by being supplied in an immune-stimulating amount to a cancer cell, comprising the identification marker according to (16) to (19).

The pharmaceutical compositions of (25) and (26) can be identified as potential therapeutic agents used for treatment of a cancer. Alternatively, the pharmaceutical compositions according to (25) and (26) can be used as therapeutic agents used for treatment of a cancer.

According to the present invention, it is possible to identify the morbidity of epithelial ovarian cancer based on a tissue-type in view of molecular typing which is different from a conventional histopathology. In other words, according to the present invention, it is possible to provide a marker for identification of a tissue-type of epithelial ovarian cancer.

The marker of the present invention was found by profiling based on identification of a protein. While profiling is generally executed by immunostaining, the profiling executed by the present inventors realizes high reliability as a marker of the found protein unlike that obtained by immunostaining where artifacts are often observed.

Furthermore, since markers of the present invention are found based on quantification of a difference in expression between tissue-types, they are clinically very persuasive. Furthermore, by using a combination of a plurality of markers, it is possible to execute analysis with higher specificity than in the case where a conventionally used broad marker having lower specificity (for example, CA-125 or CA-19-9) is used.

BRIEF DESCRIPTION OF THE DRAWINGS

FIG. 14 shows results of tissue-type classification based on expression levels of four proteins Annexin-A4 (ANXA4), Maspin precursor (MASPIN), Cellular retinoic acid-binding protein 2 (CRABP2) and Phosphoserine aminotransferase (PSAT1) which are markers of the present invention, using Western blotting.

MODES FOR CARRYING OUT THE INVENTION

Figure 1:
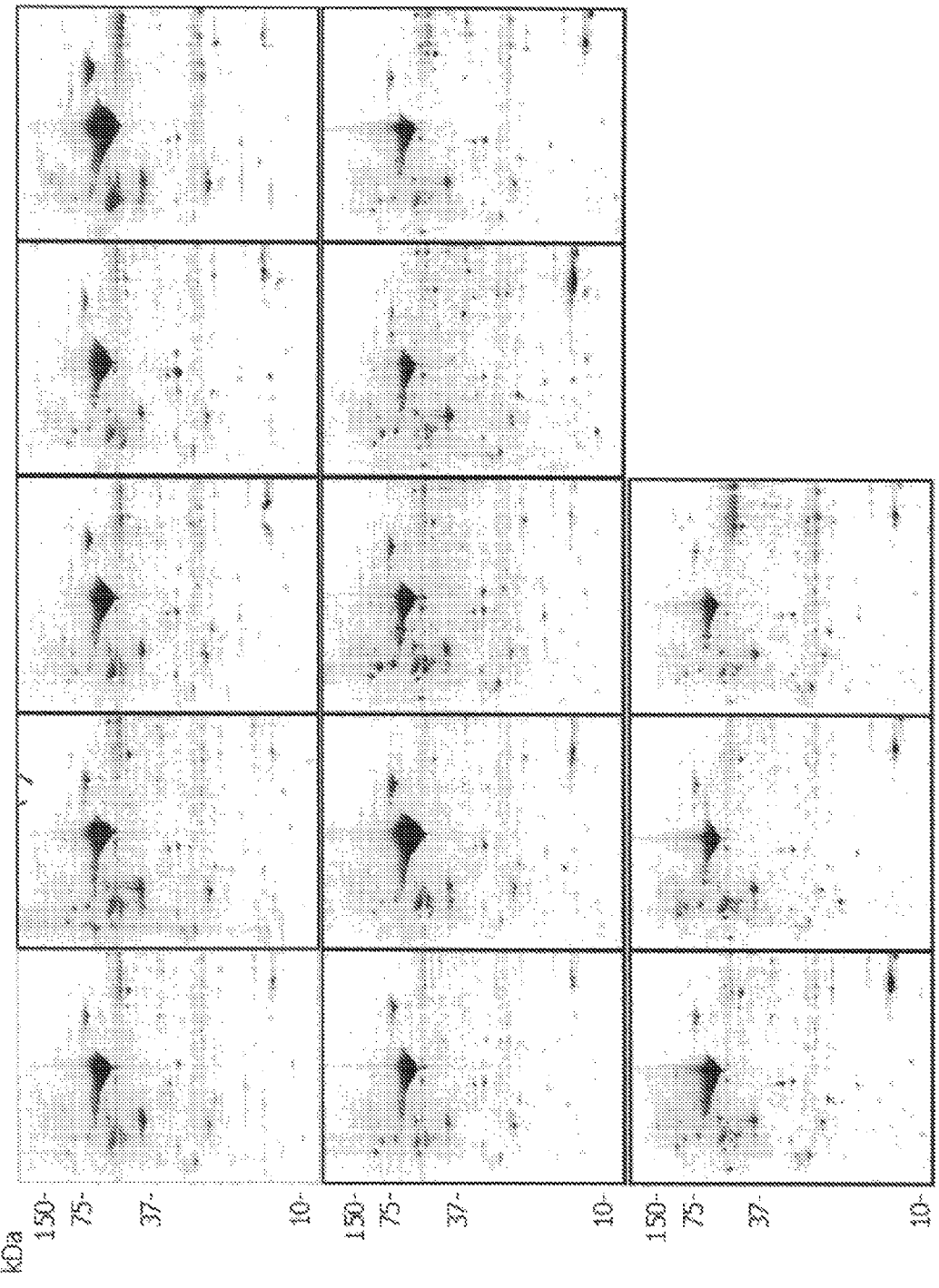
FIG. 1 shows electrophoresis diagrams of histopathological samples originated from patients suffering from Clear Cell.
Figure 2:
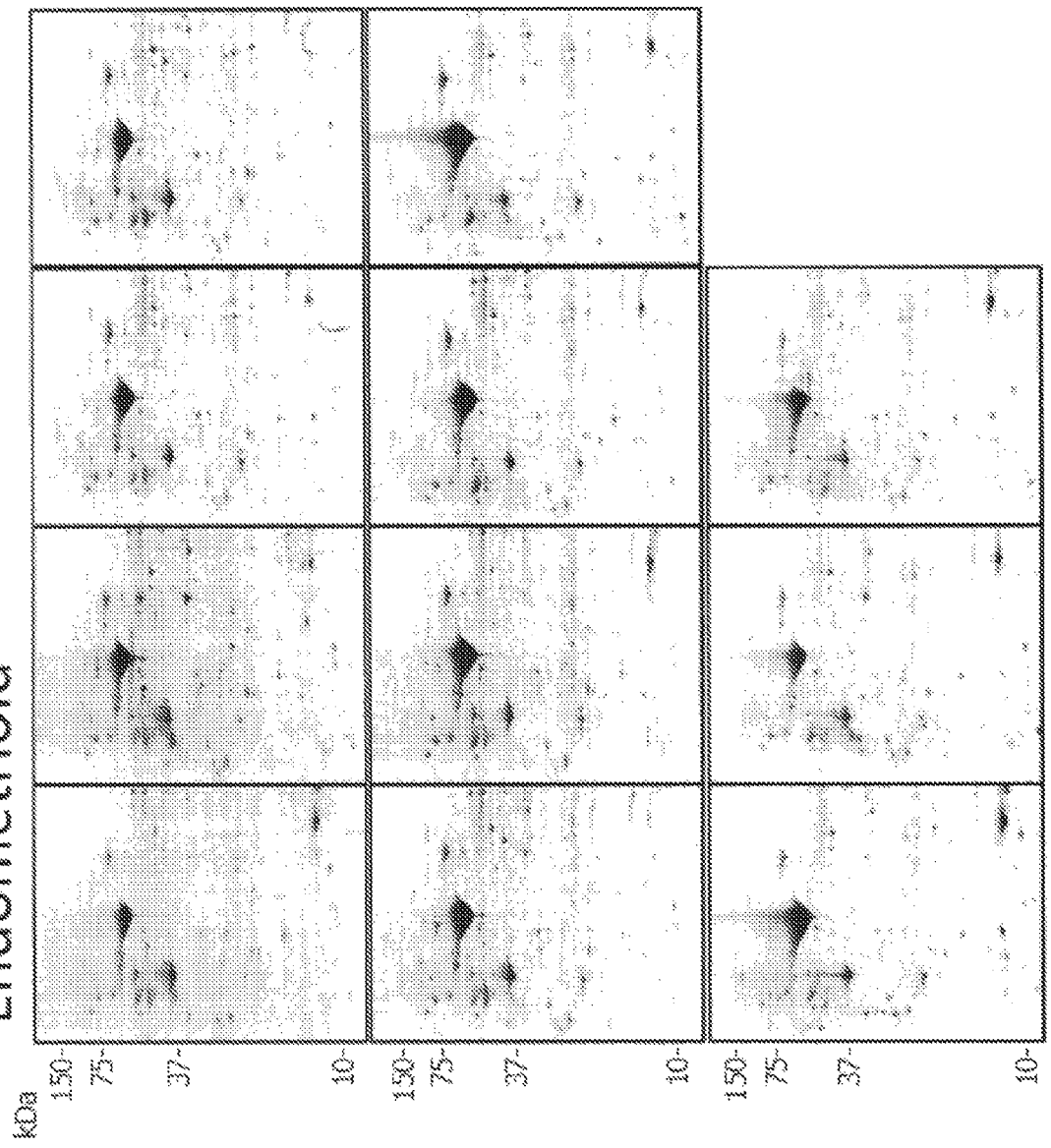
FIG. 2 shows electrophoresis diagrams of histopathological samples originated from patients suffering from Endometrioid.
Figure 3:
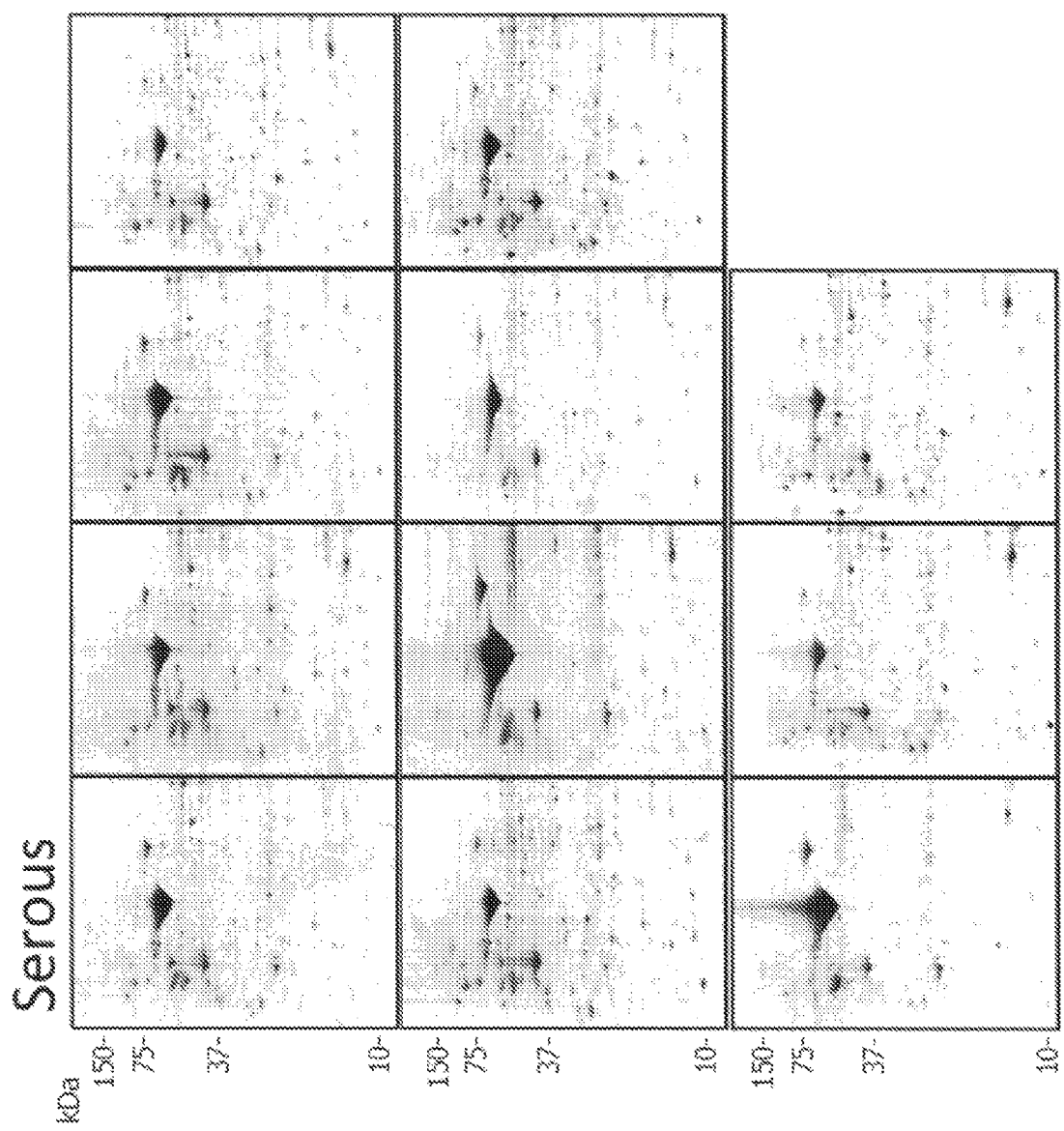
FIG. 3 shows electrophoresis diagrams of histopathological samples originated from patients suffering from Serous.
Figure 4:
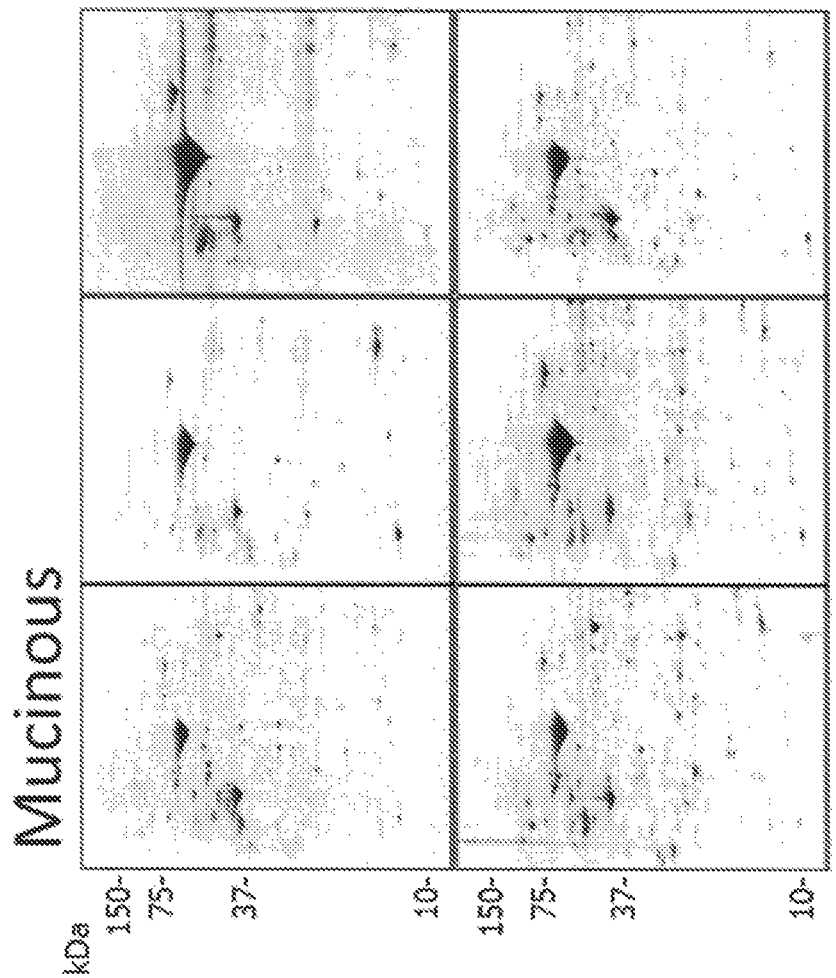
FIG. 4 shows electrophoresis diagrams of histopathological samples originated from patients suffering from Mucinous.

1. Sample to be Identified for Morbidity of Epithelial Ovarian Cancer Based on Tissue-Type In the method of the present invention, a sample originated from an individual to be identified for the morbidity of epithelial ovarian cancer is not particularly limited. For example, a cell, a tissue, a tissue extract, a bodily fluid and the like are recited. By the terms of cell and tissue, tissue biopsy materials (concretely a surgically extirpated tissue or the like), necropsy dissection materials and so on are included. By the term tissue extract, tissues that are homogenized or solubilized by methods known to those skilled in the art are included. By the term bodily fluid, blood, ascites, urine, and body secretion are included. By the term blood, whole blood, plasma, serum and the like are included. When these samples are stocked samples, the stocking environment should be −80° C. or less, in principle, and is preferably stocked in a low temperature environment using liquid nitrogen.

2. Marker for Identification of Tissue-Type

In the present invention, epithelial ovarian cancer is a target of analysis. In the samples as described above, the level of a marker for identification of a tissue-type is quantified, and whether the marker is detected in a significant amount is determined. Based on the result, a tissue-type of epithelial ovarian cancer is determined. A marker for identification of a tissue-type of the present invention is a biological molecule showing a specific expression tendency (namely, a tendency of an upregulation in expression or a downregulation in expression) in a specific tissue-type of epithelial ovarian cancer.

[2-1. Profiling for Searching Marker for Identification of Tissue-Type]

Such a biological molecule is found by conducting expression profiling from a sample originated from a patient suffering from epithelial ovarian cancer of which tissue-type is definitively diagnosed. Inherently, the basic concept of the present invention that a tissue-type is determined by using a marker for identification of a tissue-type was led by the fact that existence of a molecule showing a specific expression tendency in a specific tissue-type was clarified as a result of profiling of epithelial ovarian cancer made by the present inventors.

While the conventional profiling for search of a tumor marker conducts a variability analysis between a pathological model and a normal model, the profiling in the present invention essentially conducts a variability analysis of an expression amount between tissue-types. Therefore, a conventional profiling method may be applied except that a variability analysis is conducted between tissue-types.

First, a sample originated from a patient suffering from epithelial ovarian cancer of which tissue-type is definitively diagnosed is prepared for a plurality of tissue-types. The sample is similar to the aforementioned sample originated from an individual for whom morbidity of epithelial ovarian cancer is to be determined.

Then, quantification of an expression amount for the biological molecules group is executed for the plurality of tissue-types while a separation and purification step and an identification step of the biological molecules group expressed in the samples are included as necessary. When separation and purification and/or identification is/are executed, the concrete methodology thereof is not particularly limited. Therefore, it may be conducted by a method well-known to a person skilled in the art. Also a concrete method of quantification is not particularly limited. Therefore, it may be conducted by a method well-known to a person skilled in the art.

A quantified expression level of a biological molecule is subjected to a variability analysis between tissue-types. That is, a biological molecule whose quantified value in a specific tissue-type upregulates or downregulates relative to quantified values in other tissue-types by a significant variation amount are screened and determined from the group of biological molecules expressed in a sample. A concrete method of the variability analysis is not particularly limited. It may be appropriately conducted by a person skilled in the art according to a conventional profiling method that conducts a variability analysis between a pathological model and a normal model.

For example, a profiling method executed by the present inventors was conducted in the following manner.

From the histopathological view, using ovarian cancer clinical tissue specimens whose tissue-type are accurately diagnosed from Clear Cell, Endometrioid, Serous, and Mucinous, a protein expressed in each specimen was isolated by two-dimensional electrophoresis, and quantification by staining and identification by mass fingerprinting analysis were conducted. In a variability analysis between tissue-types, each of isolated protein spots was matched between samples, the quantified values were aggregated, and whether the average expression level in each tissue-type has a significant difference compared to that in other tissue-types was evaluated by T test. Setting a cutoff value of screening at "P value <0.005" or "P value <0.05 and an expression difference of three times or more," variable proteins satisfying the criteria were screened, and expression profiles characterizing respective tissue-types were prepared.

For conducting profiling, enormous amounts of data will be handled. Therefore, it is preferred to use an in-house data server capable of uniformly managing such data (see later-described FIG. 5). The in-house data server is preferably accessible from an individual client PC via a local network, and requires no special software, and allows a researcher to individually record experiment data. Preferably, the in-house data server is able to store and display experiment data itself, additional information, and modification on stored data. More preferably, an in-house data server is able to access public database.

When two-dimensional electrophoresis method is used in profiling, it is preferred to create a 2D map incorporating protein information retrieved into the in-house server. By using this 2D map, it is possible to facilitate the subsequent data mining. As such an in-house server, SOLPHI available from Shimadzu Corporation is preferably used.

In data mining, matching of spots obtained by two-dimensional electrophoresis is conducted, and a list can be created about spot information. The list of spot information includes intensity of a spot (namely a quantified value) and an identification result. The format of the list of spot information is a format corresponding to spreadsheet software represented by Microsoft Excel, and is preferably designed in an array style so as to conform with output data of a typical micro array. As a result, it is possible to retrieve data into software for array analysis or statistical analysis software.

Screening of protein spots is conducted by applying a filtering function of such software. A model of an expression pattern is prepared, and spots showing an approximate expression pattern may be screened based on the correlation with the model expression pattern by statistical analysis.

[2-2. Expression Pattern of Marker for Identification of Tissue-Type]

A model of an expression pattern shows a characteristic expression pattern of a protein to be screened as a protein that is to constitute an expression profile. In other words, it shows the criteria, namely the proteins should be screened in which tissue-type its specific expression is shown and with what degree the specific expression is (in other words, to what degree of upregulation or downregulation an expression amount in a certain tissue-type shows relative to an expression amount in another tissue-type). Preferably, a plurality of classified expression patterns are prepared.

In the case of profiling for finding a molecular marker for conducting identification of Clear Cell, Endometrioid, Serous, or Mucinous as a tissue-type of epithelial ovarian cancer, different expression patterns may be classified into the following 14 model expression patterns. Classification into these 14 patterns was conducted in profiling actually executed by the present inventors (see FIG. 6).

Biological molecules specifically showing an upregulation in expression in a specific one tissue-type of epithelial ovarian cancer:

<1> a protein C(+) specifically showing an upregulation in expression only in Clear Cell
<2> a protein E(+) specifically showing an upregulation in expression only in Endometrioid
<3> a protein S(+) specifically showing an upregulation in expression only in Serous
<4> a protein M(+) specifically showing an upregulation in expression only in Mucinous Biological molecules specifically showing an upregulation in expression in specific two tissue-types of epithelial ovarian cancer:

<5> a protein CS(+) specifically showing an upregulation in expression in Clear Cell and in Serous
<6> a protein CM(+) specifically showing an upregulation in expression in Clear Cell and in Mucinous
<7> a protein ES(+) specifically showing an upregulation in expression in Endometrioid and in Serous
<8> a protein SM(+) specifically showing an upregulation in expression in Serous and in Mucinous
<9> a protein CE(+) specifically showing an upregulation in expression in Clear Cell and in Endometrioid
<10> a protein EM(+) specifically showing an upregulation in expression in Endometrioid and in Mucinous Biological molecules specifically showing a downregulation in expression in a specific one tissue-type of epithelial ovarian cancer:

<11> a protein M(−) showing a downregulation in expression only in Mucinous
<12> a protein S(−) showing a downregulation in expression only in Serous
<13> a protein E(−) showing a downregulation in expression only in Endometrioid
<14> a protein C(−) showing a downregulation in expression only in Clear Cell The concrete method of statistical analysis is not particularly limited. Therefore, a person skilled in the art may appropriately determine the method for correlation and approximation analysis. Further thereafter, a test for validating statistically significant difference between tissue-types that show expression variation may be conducted. As such a test method, t test or the like may be recited. The statistically significant difference is typically P<0.05, and more preferably P<0.01.

[2-3. Markers for Identification of Tissue-Type Contained in Profile by the Present Inventors]

According to the profiling by the present inventors, a protein profile containing 80 protein markers as exemplified below was prepared.

1. Protein C(+) specifically showing an upregulation in expression only in Clear Cell
   Acid ceramidase precursor
   Alpha crystallin B chain (two kinds)
   Annexin A1 (Annexin-1)
   Annexin A4 (Annexin-4) (two kinds)
   Carbonic anhydrase 1
   Catechol O-methyltransferase
   Cellular retinoic acid-binding protein 1
   Cystathionine gamma-lyase
   Endoplasmic reticulum protein ERp29 precursor
   Ferritin heavy chain
   Glutathione peroxidase 3 precursor
   Guanine deaminase
   Laminin subunit beta-1 precursor (Laminin B1 chain)
   Laminin subunit gamma-1 precursor (Laminin B2 chain)
   L-lactate dehydrogenase B chain
   Low molecular weight phosphotyrosine protein phosphatase
   Methylcrotonoyl-CoA carboxylase beta chain, mitochondrial precursor
   Nicotinamide N-methyltransferase
   Peroxiredoxin-2
   Peroxiredoxin-6
   Phosphomannomutase 2
   Phosphoserine aminotransferase (two kinds)
   Protein SET
   Purine nucleoside phosphorylase (two kinds)
   Pyridoxal kinase
   Serum amyloid P-component precursor
   SPRY domain-containing protein 4
   Superoxide dismutase [Mn], mitochondrial precursor
   Synaptic vesicle membrane protein VAT-1 homolog
   Thioredoxin domain-containing protein 12 precursor
   Transaldolase
   Triosephosphate isomerase
   Tryptophanyl-tRNA synthetase, cytoplasmic
   Uncharacterized protein C7orf24
   (provided that, among the above C(+) markers, at least Annexin A4 (Annexin-4) is used when marker molecule quantification is conducted using a method allowing distinction between presence and absence of post-translational modification)

2. Protein E(+) specifically showing an upregulation in expression only in Endometrioid
   ASRGL1 protein
   Parvalbumin alpha 3. Protein S(+) specifically showing an upregulation in expression only in Serous
   Astrocytic phosphoprotein PEA-15
   c-Myc-responsive protein Rcl
   Cyclin-dependent kinase inhibitor 2A
   F-actin capping protein subunit alpha-1
   Gamma-synuclein (Breast cancer-specific gene 1 protein)
   Glyoxalase domain-containing protein 4
   Ras-related protein Rab-2A
   Replication protein A 32 kDa subunit
   S100 calcium-binding protein A13
   Small ubiquitin-related modifier 2 precursor (SUMO-2)
   Ubiquinol-cytochrome c reductase complex 11 kDa protein, mitochondrial precursor 4. Protein M(+) specifically showing an upregulation in expression only in Mucinous
   Fatty acid-binding protein, liver
   Serpin B5 precursor (Maspin)
   Thioredoxin (ATL-derived factor)
   Transgelin-2

5. Protein CS(+) specifically showing an upregulation in expression in Clear Cell and in Serous
   6-phosphogluconolactonase
   Ubiquinol-cytochrome-c reductase complex core protein I, mitochondrial precursor 6. Protein CM(+) specifically showing an upregulation in expression in Clear Cell and in Mucinous
   Carbonic anhydrase 2
   Delta(3,5)-Delta(2,4)-dienoyl-CoA isomerase
   Thiosulfate sulfurtransferase
   Annexin A4 (Annexin-4)
   (provided that, among the above CM(+) markers, Annexin A4 (Annexin-4) is used when marker molecule quantification is conducted using a method not allowing distinction between presence and absence of post-translational modification)

7. Protein ES(+) specifically showing an upregulation in expression in Endometrioid and in Serous
   RhoGDP-dissociation inhibitor 2
   Transgelin 8. Protein SM(+) specifically showing an upregulation in expression in Serous and in Mucinous
   Barrier-to-autointegration factor
   Cellular retinoic acid-binding protein 2
   S100 calcium-binding protein A11
   S100 calcium-binding protein A4
   S100 calcium-binding protein A6
   Selenium-binding protein 1
   Transgelin-2

9. Protein CE(+) specifically showing an upregulation in expression in Clear Cell and in Endometrioid
   Calcyphosin
   Fibrinogen beta chain precursor 10. Protein EM(+) specifically showing an upregulation in expression in Endometrioid and in Mucinous 11. Protein M(−) specifically showing a downregulation in expression only in Mucinous
    Haloacid dehalogenase-like hydrolase domain-containing protein 2

12. Protein S(−) specifically showing a downregulation in expression only in Serous 13. Protein E(−) specifically showing a downregulation in expression only in Endometrioid
    Bis(5′-nucleosyl)-tetraphosphatase [asymmetrical]
    Chloride intracellular channel protein 1
    Monoamine-sulfating phenol sulfotransferase 14. Protein C(−) specifically showing a downregulation in expression only in Clear Cell
   Acyl-CoA-binding protein
   Coactosin-like protein
   SH3 domain-binding glutamic acid-rich-like protein
   Transgelin
   Uncharacterized protein C6orf115

Among the aforementioned markers, proteins described as "(two kinds)" (namely, Alpha crystallin B chain, Annexin A4 (Annexin-4), Phosphoserine aminotransferase, and Purine nucleoside phosphorylase) are detected as completely different molecules (concretely, a post-translational modified molecule and an unmodified molecule) when detection treatment is conducted using a method allowing distinction between presence and absence of post-translational modification. On the other hand, when detection treatment is executed by using a method not allowing distinction between presence and absence of post-translational modification, these molecules are detected as the same molecule.

Therefore, in the present invention, some proteins show different expression patterns when detection treatment is conducted using a method allowing distinction between presence and absence of post-translational modification and when detection treatment is executed using a method not allowing distinction between presence and absence of post-translational modification. Among the aforementioned proteins, for example, Annexin A4 (Annexin-4) may be used as a C(+) marker when a method allowing distinction between presence and absence of post-translational modification is used, and as a CM(+) marker when a method not allowing distinction between presence and absence of post-translational modification is used.

3. Use of Marker for Identification of Tissue-Type

Identification of the morbidity of a tissue-type of epithelial ovarian cancer based on a tissue-type according to the present invention is conducted using markers for identification of a tissue-type obtained by the profiling as described above. For identifying Clear Cell, Endometrioid, Serous, and Mucinous as tissue-types of epithelial ovarian cancer, at least one biological molecule showing the expression patterns as shown in the above <1> to <14> may be used as a marker for identification of a tissue-type in the following manner.

[3-1. Use of Marker for Identification of Tissue-Type Showing Specific Expression Pattern in Specific One Tissue-Type]

As shown in the above expression patterns <1> to <4>, in the case of a biological molecule specifically showing an upregulation in expression in a specific one tissue-type, for example, knowing that C(+) is significantly detected (in other words, an upregulation in expression is shown) will by itself be a convincing index for the occurrence of clear cell cancer. Knowing that E(+) is significantly detected will by itself be a convincing index for the occurrence of endometrioid carcinoma. The same applies also to S(+) and M(+). Different biological molecules showing the same expression pattern may be used in combination.

As shown in the above expression patterns <11> to <14>, in the case of a biological molecule specifically showing a downregulation in expression in a specific one tissue-type, for example, knowing that C(−) is not significantly detected (in other words, a downregulation in expression is shown) will by itself be a convincing index for the occurrence of clear cell cancer. Knowing that E(−) is not significantly detected will by itself be a convincing index for the occurrence of endometrioid carcinoma. The same applies also to S(−) and M(−). Different biological molecules showing the same expression pattern may be used in combination.

[3-2. Use of Marker for Identification of Tissue-Type Showing Specific Expression Pattern in Specific Plural Tissue-Types]

As shown in the above expression patterns <5> to <10>, a biological molecule specifically showing an upregulation in expression in a specific plurality of tissue-types is used in combination with a biological molecule showing another expression pattern.

For example, when expression amounts are examined for CS(+) and CM(+), and both of these are found to be significantly detected, the combination is regarded as a convincing index for the occurrence of clear cell cancer.

For example, when expression amounts are examined for CS(+) and CM(+), and both of these are found not to be significantly detected, the combination is regarded as a convincing index for the occurrence of endometrioid carcinoma.

For example, when expression amounts are examined for CS(+) and C(+), and both of these are found to be significantly detected, the determination of occurrence of clear cell cancer obtained only by significant detection of C(+) is supported more reliably.

For example, when expression amounts are examined for CS(+) and C(−), and CS(+) is found to be significantly detected and C(−) is found not to be significantly detected, the determination of occurrence of clear cell cancer obtained only by no significant detection of C(−) is supported more reliably.

In this manner, when a biological molecule specifically showing an upregulation in expression in a specific plurality of tissue-types is used as an identification marker, a tissue-type may be identified by combination with any biological molecule showing another expression pattern. It goes without saying that the number of biological molecules to be combined is not limited. Concretely, 5 or more kinds, for example, 5 to 10 kinds, or 5 to 30 kinds of combinations will be preferred, although it depends on detecting and quantifying means for the marker. A combination makes it possible to identify tissue-type with high reliability.

4. Detection Treatment of Marker for Identification of Tissue-Type

A sample originated from an individual of interest is subjected to a detection treatment for a marker for identification of a tissue-type. In the detection treatment, examination of whether or not significant detection of the marker molecule is achieved (namely, quantitative analysis) is conducted while a separation and purification step or an identification step of the marker molecule is included as necessary.

[4-1. Separation and Purification of Marker for Identification of Tissue-Type]

Methods of separation and purification of a marker molecule are not particularly limited. Therefore, any technique that is selected by a person skilled in the art may be used. As such a technique, for example, electrophoresis, chromatography (for example, ion exchange, affinity, and size exclusion column chromatography and the like), centrifugation, immunoprecipitation, and separation and purification utilizing solubility difference may be recited.

[4-2. Identification of Marker for Identification of Tissue-Type]

Also a method of identification of a marker molecule is not particularly limited. Therefore, any technique that is selected by a person skilled in the art may be used. As such a technique, methods using mass spectrometry such as peptide mass finger printing may be recited.

[4-3. Quantification of Marker for Identification of Tissue-Type]

Also a method of quantification of a marker molecule is also not particularly limited. Therefore, any technique that is selected by a person skilled in the art may be used. Such a technique is arbitrarily selected from, for example, analytical methods according to various staining methods (including staining methods based on fluorescence, chemiluminescence, coloring), analytical methods based on biospecific affinity, and other quantitative analysis methods.

Various staining methods are well known to a person skilled in the art, and are not particularly limited. Therefore, a person skilled in the art may readily select a concrete staining method protocol. Various staining methods are often used as a part of a protocol of an analytical method based on biospecific affinity as will be described below.

The analytical method based on biospecific affinity is well known to those skilled in the art, and is not particularly limited. However, an immunoassay using an antibody for the marker for identification of tissue-type is preferably used. Specific examples of an immunoassay include competitive and noncompetitive assay systems such as western blotting, radioimmunoassay, ELISA, sandwich immunoassay, immunoprecipitation, precipitation reaction, gel diffusion precipitin reaction, immunodiffusion, aggregation measurement, complement binding assay, immunoradiometric assay, fluorescence immunoassay, and protein A immunoassay. Such an immunoassay is carried out to detect the presence of an antibody bound to the marker for identification of tissue-type in the sample of a person of interest. More specifically, such an immunoassay is carried out by bringing the sample into contact with an antibody in an assay medium under conditions where the marker protein for identification of tissue-type and its antibody can form an immune complex. A more specific immunoassay protocol may be easily selected by those skilled in the art.

As other quantitative analytical methods, methods using mass spectrometry may be recited. For example, mass spectrometry using isotope labeling such as an NBS (nitrobenzene sulphenyl) method or an ICAT method is a method that achieves excellent quantitative ability. A more concrete protocol of a method using mass spectrometry may be readily selected by a person skilled in the art.

Here, in the present invention, any of quantification methods allowing distinction between presence and absence of post-translational modification, and quantification methods not allowing distinction between presence and absence of post-translational modification may be used in detection treatment. As a quantification method allowing distinction between presence and absence of post-translational modification, two-dimensional electrophoresis and the like may be recited. As a quantification method not allowing distinction between presence and absence of post-translational modification, an analytical method based on biospecific affinity may be recited.

5. Examination of Whether or not Significant Detection is Achieved

Whether or not significant detection is achieved is determined by comparing a quantified value of a marker in a sample, and the reference value of the marker. A method for conducting comparison is not particularly limited. A method of conducting relative comparison, or a method capable of correlation and approximation analysis may be appropriately determined by a person skilled in the art. Since whether or not significant detection is achieved is determined by quantitative analysis, examination may be conducted in accordance with the method employed in the variability analysis of the aforementioned profiling.

An approach capable of quantifying approximation is preferred in that it is easy to accept the case where the sample of interest contains mixed tissue-types.

[5-1. Method for Using Profile]

As the reference value of a marker, a "quantified value representative of each tissue-type" (concretely an average value in each tissue-type) of the marker may be employed.

In the aforementioned profiling, with what relative significant difference between tissue-types and in what degree of level as an absolute value the marker molecule is expressed is found by actual quantification. The absolute value of the expression amount in each tissue-type found in such a manner forms a profile as a "quantified value representative of each tissue-type."

A "quantified value representative of each tissue-type" is determined in advance for each detection method by a person skilled in the art. For example, when marker detection is conducted by using two-dimensional electrophoresis from a sample of an individual of interest, data obtained by profiling that is actually executed by the present inventors (concretely, executed using two-dimensional electrophoresis) may be directly used as a "quantified value representative of each tissue-type."

Whether the quantified value of a marker in a sample originated from an individual of interest is significantly detected may be evaluated by the one of the "quantified values representative of each tissue-type" to which the quantified value is most approximate. In this manner, it is possible to achieve diagnosis/classification of a tissue-type.

Concretely, quantification is conducted on a plurality of markers, and whether the obtained quantified value is detected significantly may be evaluated by statistic process for determining comprehensive approximation with a "quantified value representative of each tissue-type." While the number of markers subjected to quantification is not particularly limited, 5 or more kinds, for example, 5 to 10 kinds, or 5 to 30 kinds may be employed.

As a concrete example of statistic process for determining approximation, calculation of a correlation coefficient, principal component analysis and the like may be recited. These concrete methods are appropriately determined by a person skilled in the art from the statistical view point. For example, in principal component analysis, correlations of a number of components are collectively converted into a two-dimensional vector, and classification is made according to the special position represented by the same. When this method is used, for example, the determination that significant detection is achieved can be made when a marker quantified value in a sample originated from an individual of interest falls within an area defined in advance by a profile, so that diagnosis/classification is achieved with the accuracy that is arbitrarily set.

[5-2. Method Utilizing Threshold]

The aforementioned method is a method for comprehensively determining approximation using a profile, and is executed by using a plurality of markers of a certain number. On the other hand, when the number of markers that may be used is small (for example, one kind to five kinds), and quantification and evaluation are conducted independently for each of the markers, a method utilizing a threshold as a reference value of a marker may be employed as will be described below.

In this method, it is preferred to use a marker having higher tissue-type specificity. The fact that a quantified value of a marker in a sample originated from an individual of interest is significantly detected may be evaluated by that the quantified value is larger (or smaller) than the threshold for the marker. In this manner, it is possible to conduct determination such as diagnosis of morbidity. This method is useful when the quantified value is compared with a quantified value in a normal sample.

Concretely, for each of available markers, a cutoff value is set using an ROC curve. The threshold of P value is arbitrarily selected by a person skilled in the art. Sensitivity at the set cutoff value is plotted on the vertical axis, and specificity is plotted on the horizontal axis, and usually a cutoff value showing good balance of sensitivity and specificity is employed. For this reason, those skilled in the art make examination separately using a number of normal samples for each marker. By examining whether a quantified value of a marker is smaller than or larger than the cutoff value that is employed in this manner, it is possible to make determination based on the definition of each marker.

6. More Concrete Embodiment of Method for Identification of Morbidity of Epithelial Ovarian Cancer Based on Tissue-Type In the following, a more concrete embodiment of the method for identification of the morbidity of epithelial ovarian cancer based on a tissue-type will be described.

[6-1. Molecular Typing of Tissue-Type Using Two-Dimensional Electrophoresis]

This method may be suitably applied to a surgically extirpated cancer tissue. Basically, it is pursuant to the method of profiling conducted by the present inventors. Therefore, it is preferred to be conducted in an automated scheme. In such a method, an extirpated cancer tissue is ground at −80° C. or less, preferably in a liquid nitrogen environment, subjected to two-dimensional electrophoresis, and a gel after development is visualized by a staining agent. A concrete protocol will be readily selected by a person skilled in the art. Among visualized spots, the spot intensity is quantified for every protein constituting the expression profile. A quantified value thus obtained is compared with the "quantified value representative of each tissue-type" (concretely, the average value in each tissue-type) complied in a database in an expression profile, and a test is conducted by statistical analysis. Concretely, a test is preferably conducted by approximation or correlation analysis. Concretely, t test and the like may be recited. In this manner, the most approximate tissue-type is determined.

[6-2. Molecular Typing of Tissue-Type Using ELISA Method (1)]

This method may be suitably applied to a surgically extirpated cancer tissue. A concrete protocol of the ELISA method may be easily selected by a person skilled in the art. Quantification may be achieved in a simple manner using an antibody against an antigen which is a protein constituting an expression profile. Not all of the proteins constituting an expression profile should be quantified, and among these a protein having high specificity or a protein having stable behavior may be appropriately selected. About 5 to 10 proteins may be selected. Also in this case, similarly to the above method 1, the obtained quantified value is compared with the "quantified value representative of each tissue-type" (concretely, the average value in each tissue-type) complied in a database in an expression profile, and a test according to statistical analysis is conducted.

[6-3. Molecular Typing of Tissue-Type Using Immune Tissue Staining Method]

This method may be suitably applied to a tissue section of a surgically extirpated cancer tissue. As a tissue section, any forms of sections including a frozen section, an embedded section by paraffin or other embedding agents, and the like are permitted. A concrete protocol of the immune tissue staining method may be easily selected by a person skilled in the art. Quantification may be achieved in a simple manner using an antibody against an antigen which is a protein constituting an expression profile. Not all of the proteins constituting an expression profile should be quantified, and among these a protein having high specificity or a protein having stable behavior may be appropriately selected. About 5 to 30 proteins may be selected. Based on the degree of staining, a pathologic part and its tissue-type may be diagnosed. Based on the "representative staining image" corresponding to the "quantified value representative of each tissue-type" complied in a database in an expression profile, a tissue-type having the most approximate degree of staining is determined by visual inspection or an image analysis tool.

[6-4. Molecular Typing of Tissue-Type Using Mass Imaging]

This method is kindred to the above method 3. It may be suitably applied to a tissue section as recited in the method 3. Using a MALDI-TOF mass spectrometer, a marker molecule is directly detected on the tissue section. Distribution of marker molecules is outputted as an image while a radiation position of laser on the tissue section is brought into correspondence with the intensity of a detected marker molecule. Based on the intensity of the marker molecule, a pathologic part and its tissue-type may be diagnosed. Also in this case, likewise the above method 1, the obtained quantified value of the marker molecule is compared with the "quantified value representative of each tissue-type" (concretely, the average value in each tissue-type) compiled in a database in an expression profile, and a test according to statistic analysis is conducted.

[6-5. Molecular Typing of Tissue-Type Using ELISA Method (2)]

This method is suitably applied to collectable bodily fluids. As a bodily fluid, blood, ascites and the like are recited as representative examples. In this method, among the proteins constituting an expression profile, a protein satisfying the following three conditions is used as a marker: detectable also from a bodily fluid; a detected molecule being originated from a cancer tissue; and an expression amount in a cancer tissue and a detection amount from a bodily fluid being correlated with each other, and quantification is conducted using an antibody against the selected protein. Also in this case, likewise the above method 1, the obtained quantified value of the marker molecule is compared with the "quantified value representative of each tissue-type" (concretely, the average value in each tissue-type) compiled in a database in an expression profile, and a test according to statistic analysis is conducted.

[6-6. Molecular Typing of Tissue-Type Using Immunoprecipitation-Mass Spectrometry]

This method is kindred to the above method 5. This is suitably applied on bodily fluids as recited in the method 5. An antibody against the marker molecule used in the above 5 as an antigen is immobilized on a carrier (preferably beads), and the marker molecule is concentrated by immunoprecipitation. The concentrated molecule with bead is subjected to MALDI-TOF mass spectrometry, and detected quantitatively. Also in this case, likewise the above method 1, the obtained quantified value of the marker molecule is compared with the "quantified value representative of each tissue-type" (concretely, the average value in each tissue-type) compiled in a database in an expression profile, and a test according to statistic analysis is conducted.

7. Others

According to the method of the present invention, the tumor marker according to the present invention may be measured alone or in combination with any other tumor marker (for example, CA-125, CA-19-9 and the like). Therefore, the method according to the present invention may include measuring the level of another tumor marker in addition to measuring the level of the tumor marker according to the present invention.

The tumor marker according to the present invention may be used for detection (screening), diagnosis, monitoring, staging, and prognostic evaluation of cancer, and is for example used to examine tumor position and its kinetics. More specifically, in the case that the tumor is treated by chemical therapy or radiation therapy, the marker may be used to grasp the position where the treatment should be made. Further, in the case that the tumor has already been treated by chemical therapy or radiation therapy, the marker may be used to determine how much effect the therapy has had. Further, in the case that the excisional surgery is operated for a tumor showing a high tumor marker level, the marker may be used for postoperative follow-up.

8. Drug Composition

It is provided that a drug composition for treatment of cancer of the specific tissue type by using the tumor marker, among the marker for identification of tissue-type in the present invention, including the protein showing upregulation in expression in the body of the patient suffering from one specific tissue type of epithelial ovarian cancer.

One embodiment of the present invention provides a drug composition to be supplied to cancer cells to induce killing of cancer cells and/or reaction promoting suppression of the growth of cancer cells, the drug composition including at least one antibody to be immunospecifically bound to the tumor marker according to the present invention. The term "antibody" includes polyclonal antibodies, monoclonal antibodies, and antibodies prepared by molecular biologic techniques. Here, the antibody widely refers to a material which has immunospecifical bounding ability. For example, antibody fragments and antibody fusion proteins may also be used. In each case, such an antibody is prepared by a method well known to those skilled in the art.

Another embodiment of the present invention provides a drug composition to be supplied to cancer cells in an immunostimulating amount to promote immune response, the drug composition including the tumor marker according to the present invention. Here, the immunostimulating amount refers to the amount of an antigen capable of inducing desired immune response for treatment of cancer, and is determined by a method well known to those skilled in the art. By using such a drug composition, it is possible to carryout treatment of cancer, known as so-called cancer vaccine therapy, by a method well known to those skilled in the art.

The above drug composition according to the present invention includes, as an active ingredient, the above-described antibody or tumor marker, but may further include a pharmaceutically acceptable diluent, carrier, excipient, or the like. The drug composition according to the present invention can be regarded as a latent therapeutic drug for use in treatment of cancer or can be used as a therapeutic drug for use in treatment of cancer.

EXAMPLES

In the following, the present invention will be concretely described by way of examples which are not intended to limit the present invention. The quantity that is represented by % is an amount based on weight/volume unless otherwise specified.

Example 1

Profiling was conducted using pathological tissues of epithelial ovarian cancer that had been excised from patients, and for which accurate tissue-type diagnosis had been made from the view point of histopathology (4 tissue-types and 41 specimens: clear cell cancer 13 specimens, endometrioid carcinoma 11 specimens, serous adenocarcinoma 11 specimens, and mucinous adenocarcinoma 6 specimens).

An excised pathological tissue (stocked in liquid nitrogen) was crushed into fragments of an appropriate size in the presence of liquid nitrogen. The crushed tissue specimen was transferred into a micro tube with a screw cap, and suspended in about 5 times weight of Lysis buffer (50 mM HEPES-NaOH pH 7.5, 100 mM NaCl, 2% CHAPS, 1% Triton X-100). The concentration in the state of a suspension was quantified by the Bradford method, and a specimen corresponding to 300 µg of protein was subjected to desalination by trichloroacetic acid precipitation, to prepare a sample for two-dimensional electrophoresis.

The washed precipitate was resolubilized by addition of 250 µL of a buffer for first dimensional isoelectric focusing electrophoresis (6 M urea, 2 M thiourea, 3% CHAPS, 1% Triton X-100, 0.5% IPG buffer, and 1.2% DeStreak Reagent). Also using the same buffer for first dimensional isoelectric focusing electrophoresis, Immobiline DryStrip, pH 3-10 NL, 13 cm (GE Healthcare) was allowed to swell over 6 hours. For the swollen strip gel, isoelectric focusing electrophoresis was conducted in the conditions of 50 V-4 hours, 150 V-1 hour, and 5000 V-17.5 hours.

After storage at −80° C., the strip gel after electrophoresis was equilibrated for 30 minutes with a equilibrating buffer (375 mM Tris-HCl pH 8.8, 6 M urea, 2% SDS, 20% glycerol), and applied to the top of a second dimensional gel (Tris-HCl 10-18% gradient, 13 cm×13 cm, 1 mm thick), and electrophoresis was conducted in the second-dimensional direction at a constant current until the dye front reached the gel end.

The gel after electrophoresis was visualized by a stain containing CBB-G250.

These steps were conducted for 4 tissue-types and 41 specimens (clear cell cancer 13 specimens, endometrioid carcinoma 11 specimens, serous adenocarcinoma 11 specimens, and mucinous adenocarcinoma 6 specimens). As representative electrophoresis images, two-dimensional electropherograms obtained from 4 tissue-types and 41 specimens are shown in FIGS. 1 to 4. Gel images were acquired in 600 dpi, 16-bit gray scale by a densitometer. Spots in the gel images was detected and quantified by a two-dimensional image analysis software. For obtaining information of expressed proteins comprehensively, a total of 10219 spots including 1530 reference spots were cut out from 11 sheets of gels, and subjected to peptide mass fingerprinting (PMF). As a result, 1139 kinds of proteins (including those identified as a mixture from one spot) were identified (P<0.05).

Figure 5:
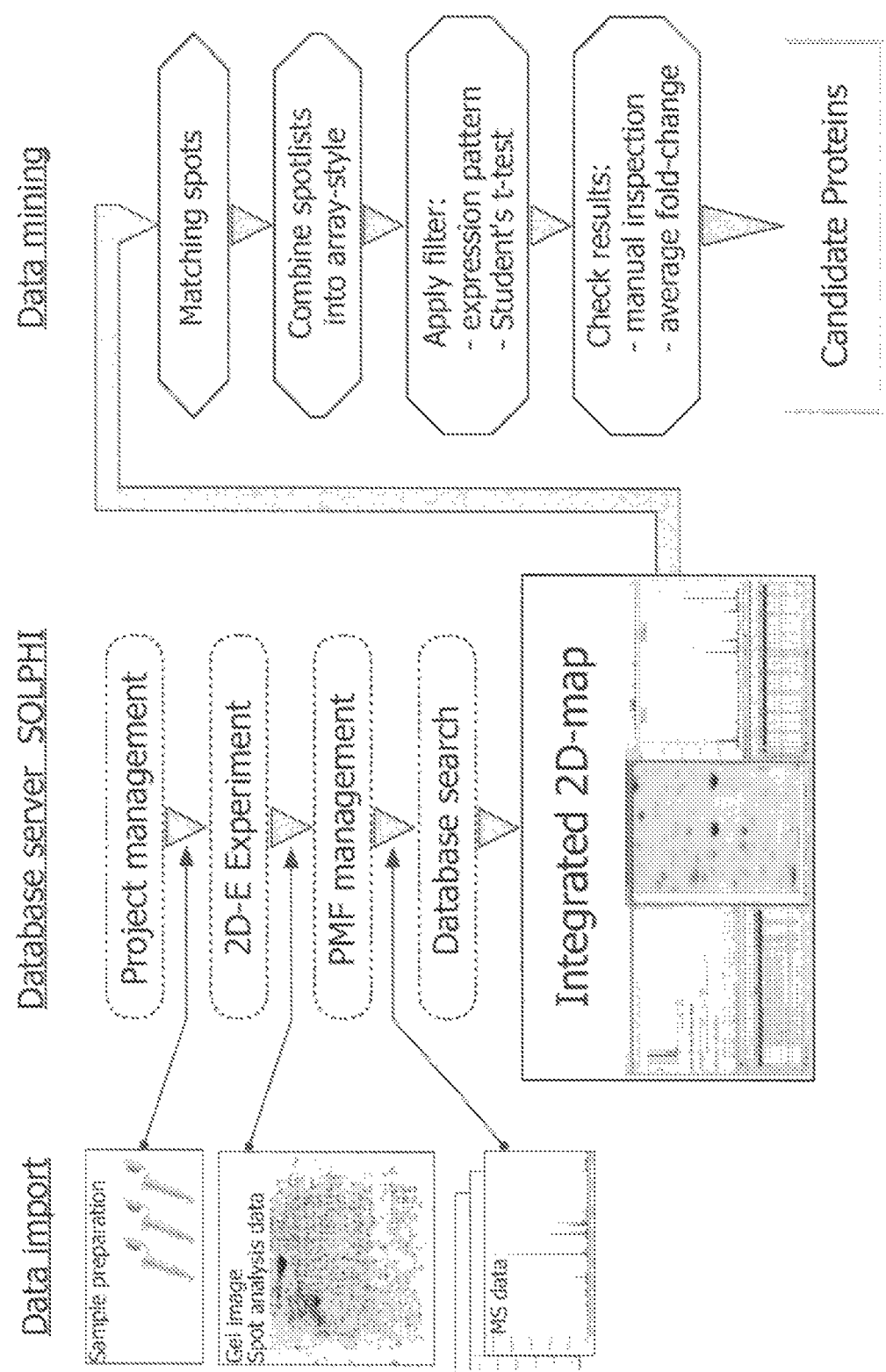
FIG. 5 is a schematic view of a profiling system.

FIG. 5 shows a schematic view of a profiling system.

Through the steps of project management, two-dimensional electrophoresis, PMF management, and database search, sample information and information about 10219 spots quantified by two-dimensional image analysis software (gel images, and spot position information on the gel), MS spectrum data, and data base search results were imported into an in-house data server (SOLPHI, available from Shimadzu Corporation). As a result, an integrated 2D map in which all necessary information about spots is visually linked was obtained for 11 specimens. This integrated 2D map is useful for subsequent data mining.

Every spot detected from each of 11 gels was subjected to matching based on a migration position and an identification result, and a list of spot intensity integrated by match ID was prepared. The spot intensity was calculated by standardization on the basis of the total intensity of a spot commonly observed in every gel, after subtraction of a background value. When a matching spot is not recognized, an expression amount of the spot was defined as ⅓ of the average value at that point of time for the convenience of analysis. This list of spot intensity was prepared concretely in an array style format wherein the reference spot ID, the accession ID and the protein name obtained as a result of PMF, the corresponding Unigene ID, and the expression amount after normalization (namely spot intensity) are aligned in line.

The prepared list of spot intensity was developed on Microsoft Excel, and the average value in each tissue-type and a T test value for evaluating whether said average has a significant difference compared to averages of other tissue-types were calculated. The test was conducted by two-tail test assuming homoscedasticity, and the significance level was set at 0.005. Also the variation width of the average value between tissue-types was calculated concurrently, and the significance level was raised to 0.05 only when the variation width was 3 times or more. A spot group that satisfies these conditions was defined as a protein that significantly varies depending on the tissue-type, and an expression profile was prepared.

Figure 6:
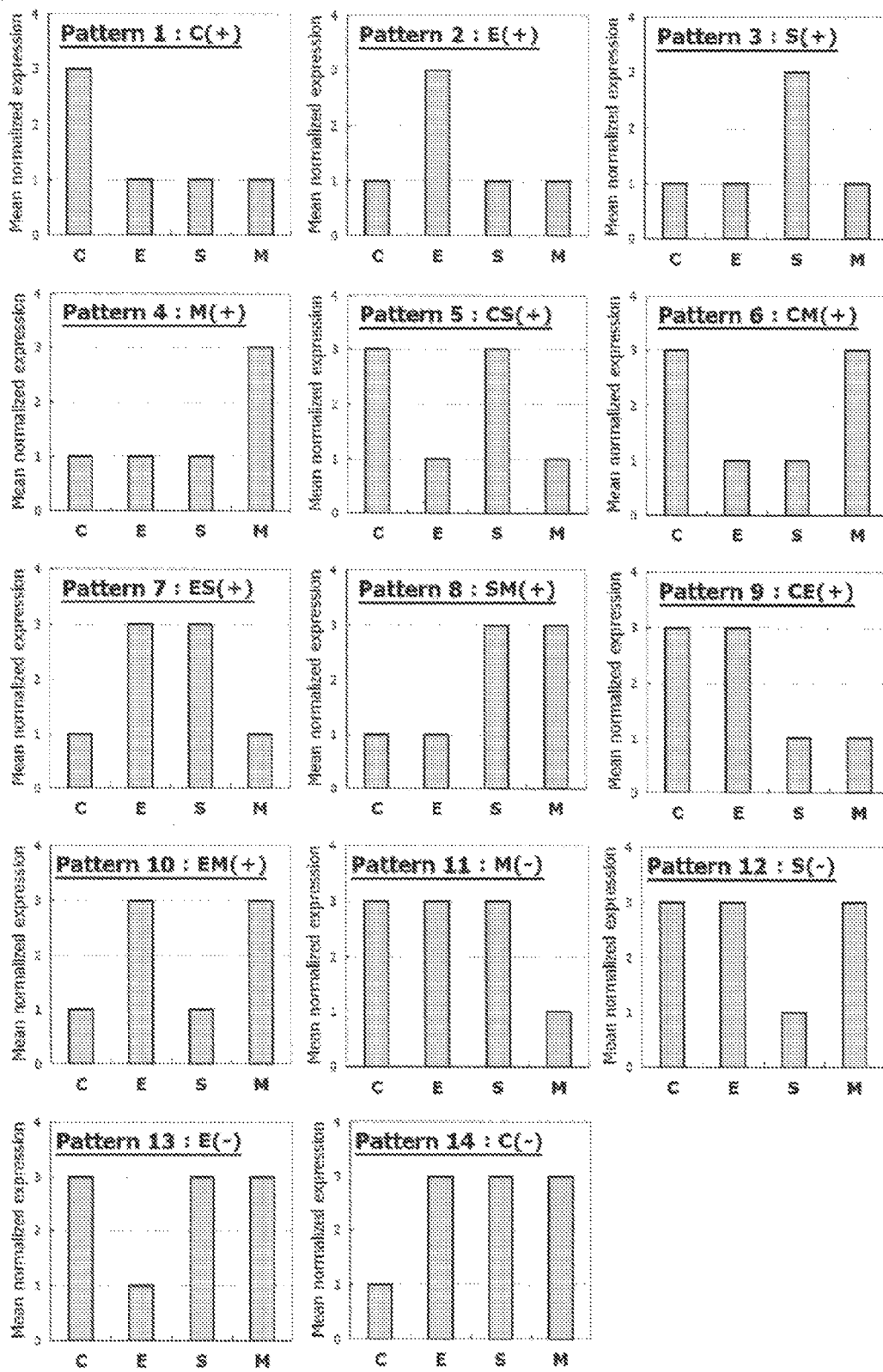
FIG. 6 shows 14 model expression patterns used in screening in the profiling.
Figure 7:
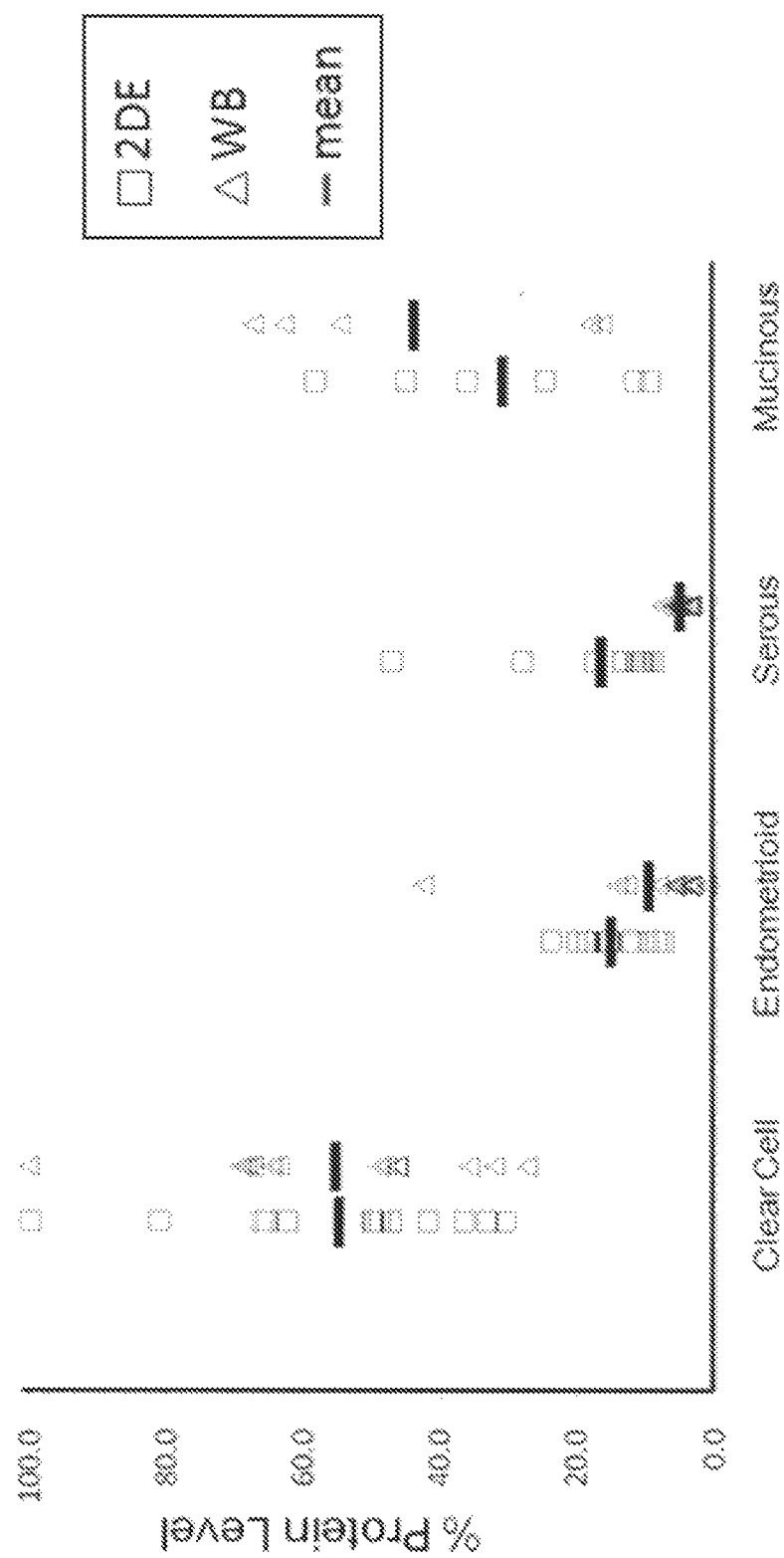
FIG. 7 is a one-dimensional scatter chart showing expression amounts of Annexin-A4 which is a marker of the present invention and specifically shows expression for Clear Cell, for different tissue-types.
Figure 8:
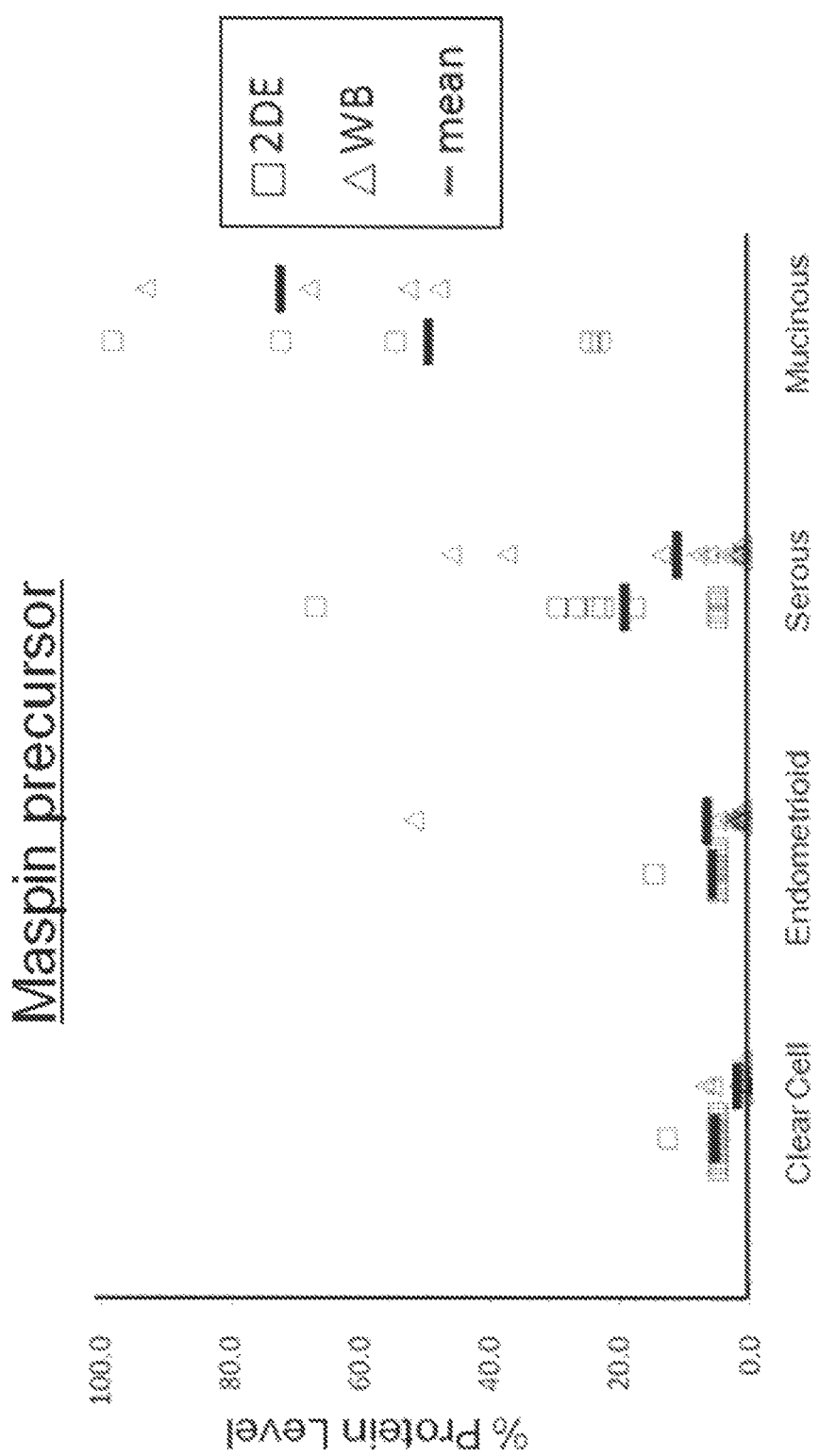
FIG. 8 is a one-dimensional scatter chart showing expression amounts of Maspin precursor which is a marker of the present invention and specifically shows expression for mucinous adenocarcinoma, for different tissue-types.
Figure 9:
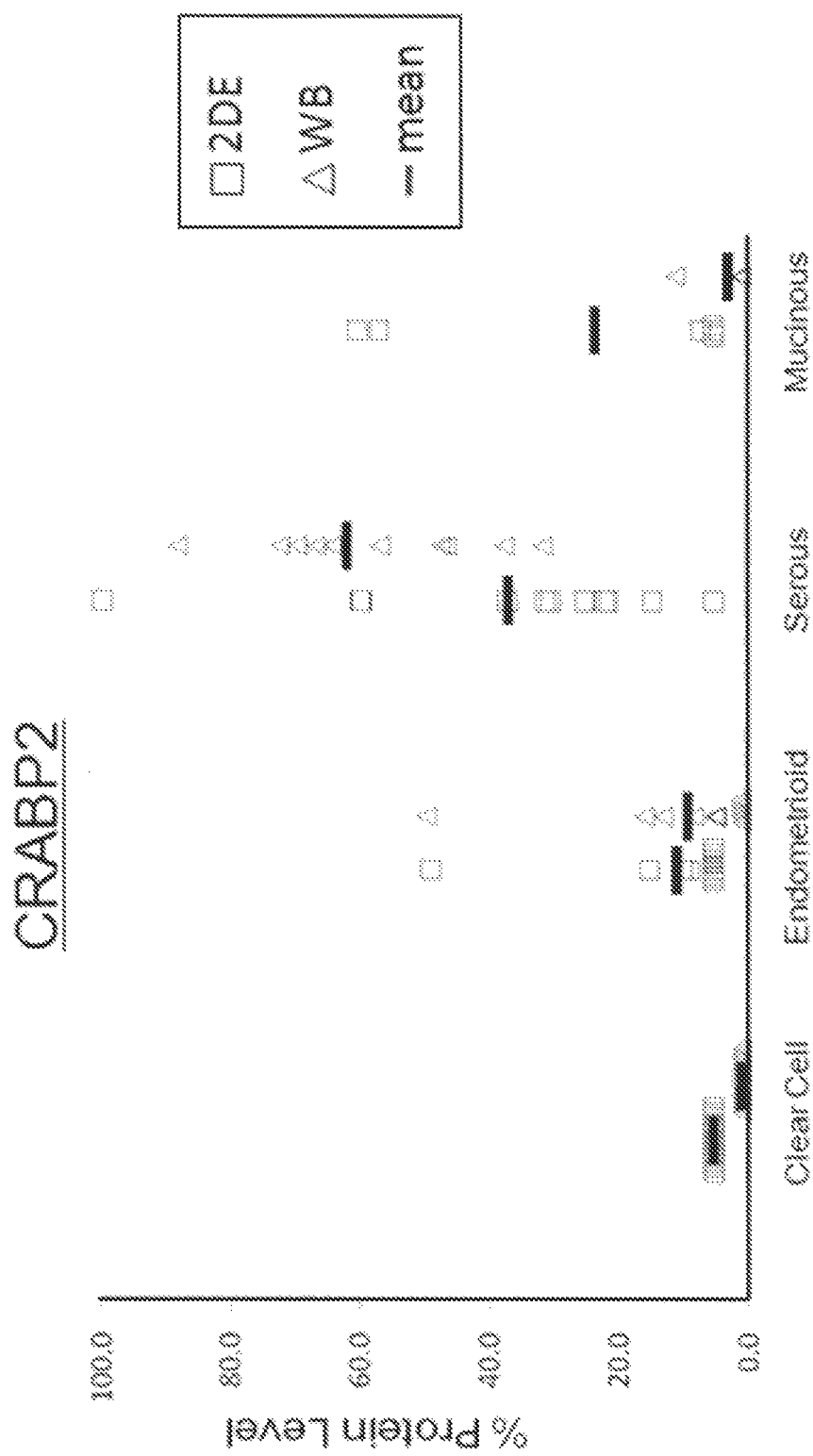
FIG. 9 is a one-dimensional scatter chart showing expression amounts of Cellular retinoic acid-binding protein 2 (CRABP2) which is a marker of the present invention and specifically shows expression for serous adenocarcinoma and mucinous adenocarcinoma, for different tissue-types.
Figure 10:
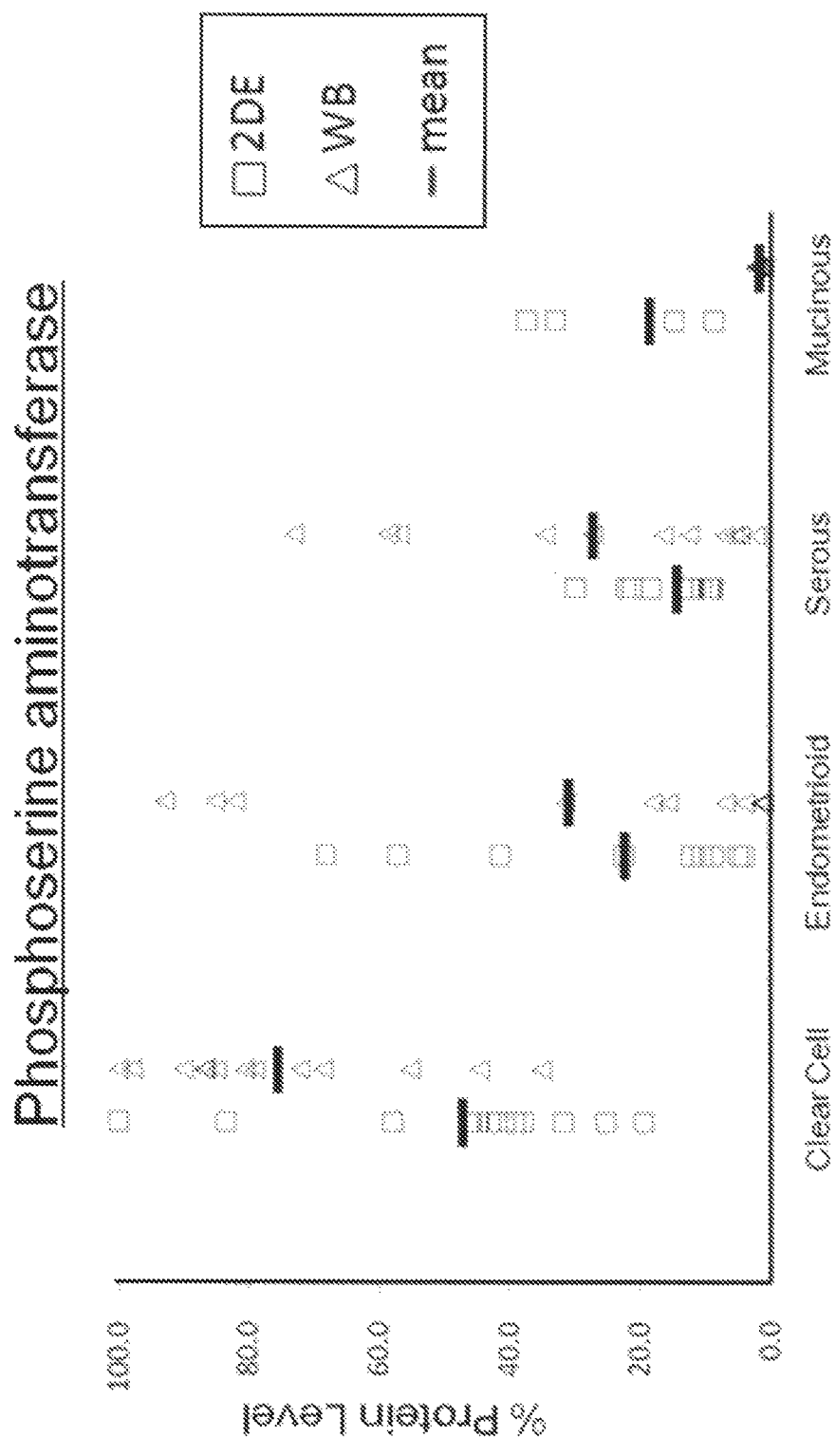
FIG. 10 is a one-dimensional scatter chart showing expression amounts of Phosphoserine aminotransferase which is a marker of the present invention and specifically shows expression for Clear Cell, for different tissue-types.

Concretely, as shown in FIG. 6, different expression patterns were roughly classified into 14 model expression patterns (Pattern 1 to Pattern 14). In FIG. 6, C represents Clear Cell, E represents Endometrioid, S represents Serous, and M represents Mucinous. The vertical axis represents a model relative amount of the average value of the normalized expression amount (Mean normalized expression). To which expression pattern each spot belongs is determined in such a way that it belongs to the hypothesis where the probability of rejection is lowest when a test is conducted by forming an alternative hypothesis for every expression pattern. For example, Pattern 1 has a definition that "expression is upregulated significantly in Clear Cell," and a test value was determined for an alternative hypothesis that "an average in a Clear Cell sample is larger than the average of all other samples." If this test value is lower than those obtained from other 13 patterns, this spot is regarded as showing specifically upregulated expression in Clear Cell.

By preparing such a work sheet that automatically executes the above calculation for every spot, the inventors constructed a system capable of defining an expression pattern of the spot and determining whether it is significant in a simple manner. The aforementioned variation width of the average value between tissue-types was calculated according to the expression pattern of each spot.

Profiles of screened 80 candidate proteins are shown in Tables 1 to 3. In Tables 1 to 3, expression patterns (Pattern) of screened proteins; accession IDs of proteins identified by PMF (Accession) and protein names (Protein Name); respective expression amounts after normalization of clear cell type (Clear Cell), endometrioid carcinoma type (Endometrioid), serous adenocarcinoma type (Serous), and mucinous adenocarcinoma type (Mucinous), (hereinafter, simply referred to as expression amounts); expression variation widths (Fold-change) and P values in T test (t-test) are shown. A protein described in plural times in Table 1 is separated in a completely different position on a gel due to post-translational modification such as phosphorylation, and treated herein as a separate molecule.

TABLE 1

| Pattern | Accession | Protein Name | Clear Cell | Endometrioid | Serous | Mucinous | Fold-change | t-test |
|---|---|---|---|---|---|---|---|---|
| C (+) | Q13510 | Acid ceramidase precursor | 13.39 | 7.36 | 4.05 | 3.97 | 2.64 | 8.73E−05 |
| C (+) | P02511 | Alpha crystallin B chain | 4.32 | 0.31 | 1.06 | 0.12 | 17.64 | 4.69E−02 |
| C (+) | P02511 | Alpha crystallin B chain | 18.22 | 2.24 | 3.60 | 2.24 | 6.58 | 3.36E−03 |
| C (+) | P04083 | Annexin A1 (Annexin-1) | 15.73 | 11.14 | 9.39 | 10.87 | 1.51 | 4.52E−03 |
| C (+) | P09525 | Annexin A4 (Annexin-4) | 39.54 | 4.90 | 9.06 | 19.85 | 4.98 | 4.83E−04 |
| C (+) | P09525 | Annexin A4 (Annexin-4) | 103.82 | 34.06 | 33.76 | 60.64 | 2.66 | 6.29E−08 |
| C (+) | P00915 | Carbonic anhydrase 1 | 39.16 | 28.57 | 22.61 | 26.19 | 1.52 | 3.84E−03 |
| C (+) | P21964 | Catechol O-methyltransferase | 14.96 | 11.24 | 9.84 | 9.77 | 1.44 | 3.23E−03 |
| C (+) | P29762 | Cellular retinoic acid-binding protein 1 | 19.32 | 7.40 | 4.12 | 6.27 | 3.29 | 4.86E−03 |
| C (+) | P32929 | Cystathionine gamma-lyase | 18.58 | 11.24 | 6.69 | 6.55 | 2.29 | 5.06E−04 |
| C (+) | P30040 | Endoplasmic reticulum protein ERp29 precursor | 31.91 | 18.35 | 16.98 | 14.68 | 1.87 | 2.71E−04 |
| C (+) | P02794 | Ferritin heavy chain | 15.12 | 11.09 | 10.51 | 6.59 | 1.88 | 9.17E−04 |
| C (+) | P22352 | Glutathione peroxidase 3 precursor | 10.93 | 4.90 | 4.92 | 5.13 | 2.20 | 1.72E−04 |
| C (+) | Q9Y2T3 | Guanine deaminase | 25.30 | 9.64 | 5.21 | 10.76 | 3.19 | 1.24E−05 |
| C (+) | P07942 | Laminin subunit beta-1 precursor (Laminin B1 chain) | 13.18 | 3.84 | 2.23 | 2.46 | 4.52 | 4.73E−06 |
| C (+) | P11047 | Laminin subunit gamma-1 precursor (Laminin B2 chain) | 17.73 | 3.83 | 6.42 | 6.33 | 3.29 | 8.24E−05 |
| C (+) | P07195 | L-lactate dehydrogenase B chain | 78.42 | 52.84 | 51.53 | 38.92 | 1.59 | 3.94E−05 |
| C (+) | P24666 | Low molecular weight phosphotyrosine protein phosphatase | 8.55 | 3.29 | 5.11 | 2.36 | 2.46 | 1.92E−03 |
| C (+) | Q9HCC0 | Methylcrotonoyl-CoA carboxylase beta chain, mitochondrial precursor | 19.11 | 13.61 | 8.22 | 9.85 | 1.89 | 3.37E−03 |
| C (+) | P40261 | Nicotinamide N-methyltransferase | 16.89 | 8.47 | 9.67 | 5.25 | 2.28 | 3.24E−03 |
| C (+) | P32119 | Peroxiredoxin-2 | 19.89 | 9.26 | 9.64 | 5.27 | 2.53 | 2.77E−04 |
| C (+) | P30041 | Peroxiredoxin-6 | 10.65 | 6.59 | 6.24 | 5.82 | 1.69 | 4.92E−03 |
| C (+) | O15305 | Phosphomannomutase 2 | 13.55 | 10.23 | 9.07 | 9.36 | 1.41 | 3.61E−03 |
| C (+) | Q9Y617 | Phosphoserine aminotransferase | 28.24 | 13.36 | 8.57 | 11.09 | 2.57 | 2.93E−05 |
| C (+) | Q9Y617 | Phosphoserine aminotransferase | 8.27 | 2.02 | 1.75 | 2.26 | 4.21 | 2.86E−05 |
| C (+) | Q01105 | Protein SET | 14.31 | 6.63 | 8.20 | 4.63 | 2.15 | 1.62E−03 |
| C (+) | P00491 | Purine nucleoside phosphorylase | 7.53 | 2.47 | 3.23 | 3.82 | 2.46 | 3.17E−04 |
| C (+) | P00491 | Purine nucleoside phosphorylase | 31.77 | 14.28 | 10.94 | 15.03 | 2.42 | 3.53E−07 |
| C (+) | O00764 | Pyridoxal kinase | 29.26 | 17.18 | 16.42 | 11.24 | 1.91 | 2.09E−05 |

TABLE 1-continued

| Pattern | Accession | Protein Name | Clear Cell | Endometrioid | Serous | Mucinous | Fold-change | t-test |
|---|---|---|---|---|---|---|---|---|
| C (+) | P02743 | Serum amyloid P-component precursor | 14.50 | 9.77 | 6.59 | 7.09 | 1.82 | 4.98E-03 |
| C (+) | Q8WW59 | SPRY domain-containing protein 4 | 22.13 | 15.71 | 13.10 | 10.14 | 1.70 | 6.93E-04 |
| C (+) | P04179 | Superoxide dismutase [Mn], mitochondrial precursor | 60.61 | 32.42 | 25.20 | 18.00 | 2.29 | 1.30E-05 |
| C (+) | Q99536 | Synaptic vesicle membrane protein VAT-1 homolog | 17.51 | 8.80 | 10.14 | 12.08 | 1.75 | 1.12E-04 |
| C (+) | O95881 | Thioredoxin domain-containing protein 12 precursor | 9.13 | 4.76 | 4.47 | 4.18 | 2.02 | 2.73E-03 |
| C (+) | P37837 | Transaldolase | 16.00 | 9.56 | 8.50 | 8.07 | 1.81 | 1.06E-03 |

TABLE 2

| Pattern | Accession | Protein Name | Clear Cell | Endometrioid | Serous | Mucinous | Fold-change | t-test |
|---|---|---|---|---|---|---|---|---|
| C (+) | P60174 | Triosephosphate isomerase | 35.59 | 15.33 | 16.76 | 12.73 | 2.32 | 4.41E-08 |
| C (+) | P23381 | Tryptophanyl-tRNA synthetase, cytoplasmic | 6.23 | 1.24 | 1.99 | 1.00 | 4.20 | 8.10E-07 |
| C (+) | O75223 | Uncharacterized protein C7orf24 | 5.95 | 1.67 | 1.27 | 2.74 | 3.41 | 1.68E-02 |
| E (+) | Q6P1P0 | ASRGL1 protein | 2.91 | 10.03 | 3.18 | 3.08 | 3.30 | 7.23E-04 |
| E (+) | P20472 | Parvalbumin alpha | 3.85 | 11.75 | 1.52 | 1.52 | 4.90 | 2.17E-02 |
| S (+) | Q15121 | Astrocytic phosphoprotein PEA-15 | 1.00 | 2.78 | 4.79 | 1.00 | 3.79 | 7.25E-03 |
| S (+) | O43598 | c-Myc-responsive protein Rcl | 3.23 | 2.86 | 6.87 | 3.58 | 2.17 | 1.81E-04 |
| S (+) | R42771 | Cyclin-dependent kinase inhibitor 2A | 1.35 | 1.00 | 4.32 | 1.98 | 3.20 | 1.07E-04 |
| S (+) | P52907 | F-actin capping protein subunit alpha-1 | 15.72 | 20.01 | 25.55 | 20.13 | 1.41 | 2.14E-03 |
| S (+) | O76070 | Gamma-synuclein (Breast cancer-specific gene 1 protein) | 1.34 | 1.34 | 8.25 | 1.34 | 6.16 | 1.76E-03 |
| S (+) | Q9HC38 | Glyoxalase domain-containing protein 4 | 2.07 | 1.68 | 6.35 | 1.00 | 3.71 | 4.96E-03 |
| S (+) | P61019 | Ras-related protein Rab-2A | 1.36 | 1.61 | 4.92 | 1.00 | 3.57 | 3.43E-03 |
| S (+) | P15927 | Replication protein A 32 kDa subunit | 3.02 | 3.65 | 5.35 | 3.37 | 1.61 | 2.55E-03 |
| S (+) | Q99584 | S100 calcium-binding protein A13 | 3.28 | 4.40 | 10.05 | 4.52 | 2.55 | 1.15E-03 |
| S (+) | P61956 | Small ubiquitin-related modifier 2 precursor (SUMO-2) | 12.24 | 13.27 | 19.93 | 13.05 | 1.56 | 1.40E-03 |
| S (+) | P07919 | Ubiquinol-cytochrome c reductase complex 11 kDa protein, mitochondrial | 1.48 | 1.75 | 4.80 | 1.00 | 3.24 | 7.82E-03 |
| M (+) | P07148 | Fatty acid-binding protein, liver | 1.09 | 1.09 | 3.73 | 11.70 | 6.10 | 2.43E-02 |
| M (+) | P36952 | Serpin B5 precursor (Maspin) | 2.09 | 3.20 | 6.97 | 19.76 | 4.98 | 1.69E-06 |
| M (+) | P10599 | Thioredoxin (ATL-derived factor) | 3.66 | 5.97 | 4.87 | 14.55 | 3.05 | 9.51E-05 |
| M (+) | P37802 | Transgelin-2 | 0.78 | 0.71 | 0.90 | 3.03 | 3.83 | 4.00E-05 |
| CS (+) | O95336 | 6-phosphogluconolactonase | 3.97 | 1.00 | 2.97 | 1.00 | 3.51 | 3.71E-02 |
| CS (+) | P31930 | Ubiquinol-cytochrome-c reductase complex core protein I, mitochondrial p | 24.13 | 15.56 | 24.74 | 17.30 | 1.51 | 3.23E-03 |
| CM (+) | P00918 | Carbonic anhydrase 2 | 43.05 | 17.68 | 23.61 | 34.08 | 1.95 | 1.08E-03 |
| CM (+) | Q13011 | Delta(3,5)-Delta(2,4)-dienoyl-CoA isomerase | 8.22 | 2.32 | 3.06 | 6.02 | 2.80 | 2.16E-02 |
| CM (+) | Q16762 | Thiosulfate sulfurtransferase | 12.75 | 7.73 | 6.31 | 14.28 | 1.89 | 2.78E-03 |
| ES (+) | P52566 | Rho GDP-dissociation inhibitor 2 | 15.24 | 18.18 | 21.00 | 11.98 | 1.50 | 3.22E-03 |
| ES (+) | Q01995 | Transgelin | 0.51 | 2.25 | 1.38 | 0.30 | 4.39 | 4.27E-02 |
| SM (+) | O75531 | Barrier-to-autointegration factor | 2.09 | 3.13 | 6.67 | 10.23 | 3.09 | 1.00E-03 |
| SM (+) | P29373 | Cellular retinoic acid-binding protein 2 | 2.97 | 6.11 | 20.71 | 13.14 | 4.50 | 1.88E-04 |
| SM (+) | P31949 | S100 calcium-binding protein A11 | 2.43 | 3.23 | 7.02 | 5.14 | 2.27 | 1.59E-03 |
| SM (+) | P26447 | S100 calcium-binding protein A4 | 3.86 | 5.02 | 15.30 | 14.18 | 3.39 | 4.61E-03 |
| SM (+) | P06703 | S100 calcium-binding protein A6 | 40.81 | 37.61 | 66.78 | 71.33 | 1.74 | 1.04E-03 |
| SM (+) | Q13228 | Selenium-binding protein 1 | 13.74 | 18.34 | 25.90 | 24.50 | 1.65 | 2.25E-03 |
| SM (+) | P37802 | Transgelin-2 | 2.39 | 3.44 | 7.78 | 9.92 | 2.97 | 6.65E-04 |
| CE (+) | Q13938 | Calcyphosin | 24.06 | 20.58 | 9.50 | 5.18 | 3.55 | 1.48E-03 |

TABLE 3

| Pattern | Accession | Protein Name | Clear Cell | Endometrioid | Serous | Mucinous | Fold-change | t-test |
|---|---|---|---|---|---|---|---|---|
| CE (+) | P02675 | Fibrinogen beta chain precursor | 10.64 | 8.72 | 5.39 | 2.27 | 3.69 | 1.17E-02 |
| M (−) | Q9H0R4 | Haloacid dehalogenase-like hydrolase domain-containing protein 2 | 3.91 | 3.01 | 2.80 | 1.08 | 3.04 | 2.97E-02 |
| E (−) | P50583 | Bis(5′-nucleosyl)-tetraphosphatase [asymmetrical] | 5.17 | 2.10 | 5.26 | 4.23 | 2.39 | 2.25E-02 |
| E (−) | O00299 | Chloride intracellular channel protein 1 | 28.86 | 18.93 | 31.54 | 27.45 | 1.56 | 1.87E-03 |
| E (−) | P50224 | Monoamine-sulfating phenol sulfotransferase | 7.86 | 4.00 | 6.82 | 11.18 | 2.04 | 9.61E-03 |
| C (−) | P07108 | Acyl-CoA-binding protein | 12.07 | 18.24 | 20.89 | 21.42 | 1.65 | 3.12E-03 |
| C (−) | Q14019 | Coactosin-like protein | 6.82 | 11.25 | 13.05 | 12.83 | 1.80 | 9.23E-05 |
| C (−) | O75368 | SH3 domain-binding glutamic acid-rich-like protein | 7.21 | 10.91 | 12.27 | 13.22 | 1.66 | 3.70E-05 |
| C (−) | Q01995 | Transgelin | 1.64 | 5.10 | 7.67 | 8.31 | 4.15 | 4.04E-02 |
| C (−) | Q9P1F3 | Uncharacterized protein C6orf115 | 1.61 | 5.19 | 3.96 | 3.55 | 2.70 | 1.16E-03 |

Among these, for Annexin A4, Maspin precursor, Cellular retinoic acid-binding protein 2 (CRABP2), and Phosphoserine aminotransferase that showed particularly high specificity, one-dimensional scatter charts showing the normalized expression amount (Protein level) for each tissue-type are shown in FIGS. 7, 8, 9 and 10, respectively. In the Figs, points plotted in the form of square represent values quantified by spots of two-dimensional electrophoresis (2DE), points plotted in the form of triangle represent values quantified by Western blotting (WB) (as will be described later), and bars represent average values (mean).

Using the above profile, it is possible to conduct tissue-type molecular typing about tissues whose tissue-type is unknown. This method may be readily determined by a person skilled in the art according to the method of profiling as described above. To be more specific, for the tissue whose tissue-type is unknown, two-dimensional electrophoresis and peptide mass finger printing are conducted similarly to the above, to conduct quantitative analysis for proteins constituting the profile of Table 1. In quantitative analysis, quantification and correlation approximation analysis may be executed in the same manner as in the above profiling except that amounts in Table 1 are used as reference amounts.

Example 2

For screening the above-described 80 candidate markers into molecules having a determinative role in diagnosing a tissue-type of an unknown ovarian cancer tissue using a molecular technique, a classification prediction model using a decision tree was constructed using statistical analysis software SPSS (SPSS Inc.). Four tissue-types were used as dependent variables, and quantified values of 80 spots of candidate markers scaled into three stages (low expression, high expression, extra-high expression) were used as independent variables. The reference value in scaling was appropriately determined based on the expression pattern and the average quantified value of each candidate marker determined by profiling.

Figure 11:
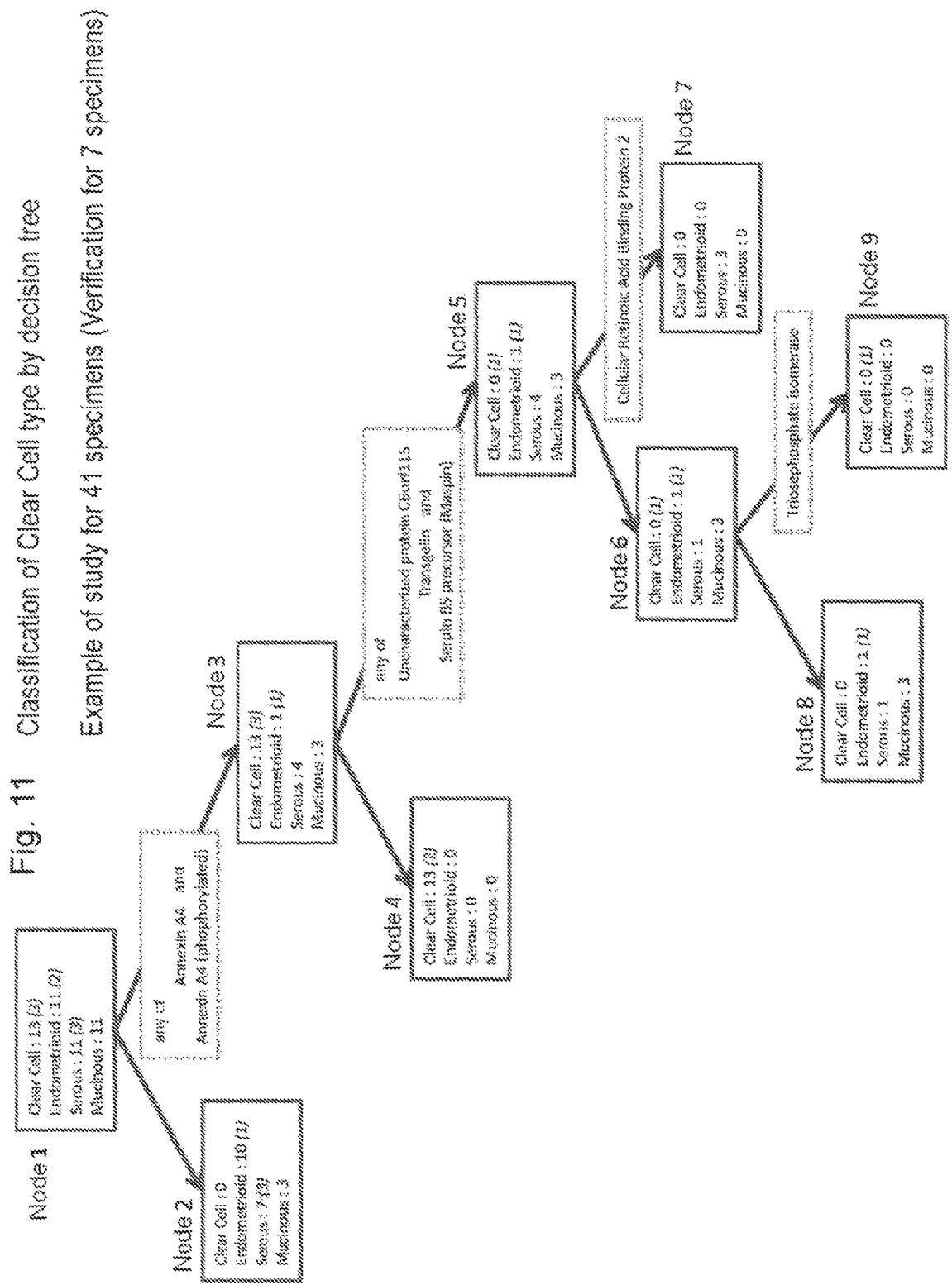
FIG. 11 is a decision tree for determining an unknown ovarian cancer tissue as Clear Cell, prepared by using markers of the present invention.

As one example, FIG. 11 shows a decision tree model for determining whether an unknown specimen is Clear Cell, prepared by using 41 specimens from which the profile was prepared. In FIG. 11, a protein used as a variable of divergence is shown inside the dashed line, and sample groups in which expression thereof is high are collected in nodes of right direction. If this model is valid, specimens of Clear Cell are aggregated into Node 4 or Node 9, and can be easily distinguished from other tissue-types.

Verification of the model was conducted using 7 specimens that are separate from 41 specimens used in Example 1. For each specimen for verification, the tissue-type was diagnosed in advance similarly to other ones, and related spots were quantified by being subjected to two-dimensional electrophoresis similarly. This was assigned to the previously described decision tree model, and classification was conducted. Determination was made correctly for all of 7 specimens. The classification result of specimens for verification is shown in oblique type in parenthesis of each node in FIG. 11.

Further, for the sample group that was not determined as Clear Cell in this decision tree, stepwise determinations can be made from Endometrioid, Serous, and Mucinous by recursively applying a similar decision tree. For example, it is easy to construct a system that automatically diagnoses the tissue-type only by inputting quantified values of 10 to 20 proteins.

Example 3

Using tissue extracts (excluding one specimen of mucinous adenocarcinoma) that are the same with those subjected to two-dimensional electrophoresis in Example 1, quantitative detection by Western blotting was conducted. As antibodies, anti-Annexin-A4 (D-2, Santa Cruz Biotechnology), anti-Maspin precursor (G167-70, BD Transduction Laboratories), anti-Cellular retinoic acid-binding protein 2 (Bethyl Laboratories) and anti-Phosphoserine aminotransferase (Proteintech Group Inc.) were used.

Figure 12:
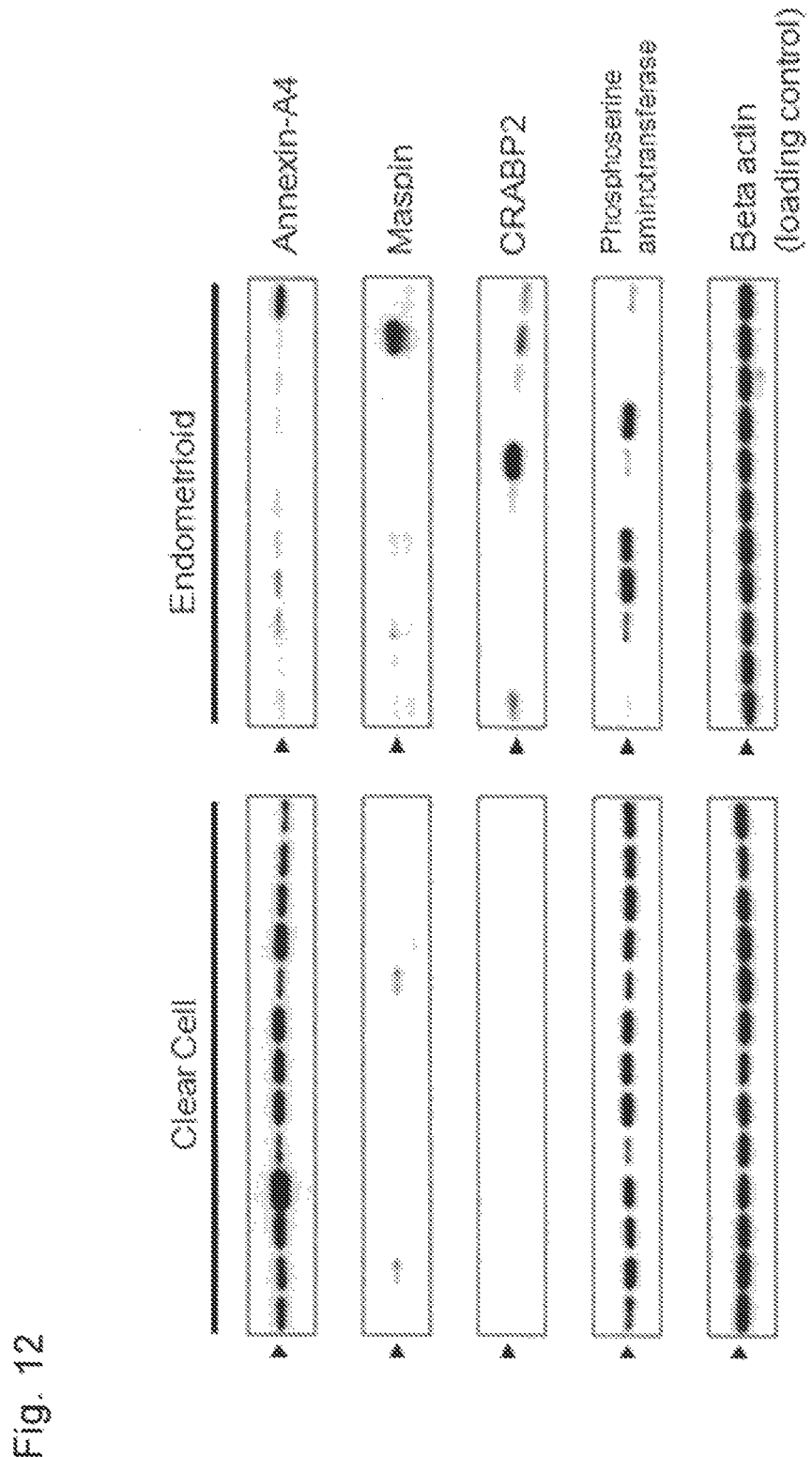
FIG. 12 shows results of Western blotting showing expression amounts in each of 40 specimens of Clear Cell and Endometrioid, by markers of the present invention, Annexin-A4, Maspin precursor, Cellular retinoic acid-binding protein 2 (CRABP2) and Phosphoserine aminotransferase.
Figure 13:
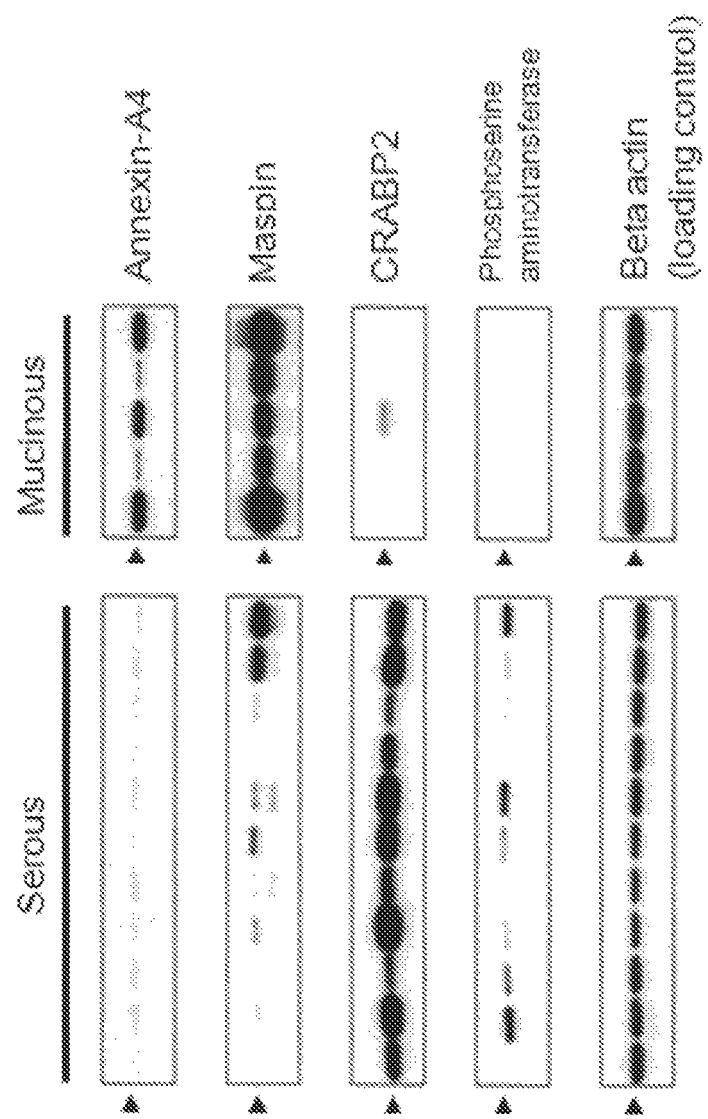
FIG. 13 shows results of Western blotting showing expression amounts in each of 40 specimens of Serous and Mucinous, by markers of the present invention, Annexin-A4, Maspin precursor, Cellular retinoic acid-binding protein 2 (CRABP2) and Phosphoserine aminotransferase.

Results of Western blotting by 40 specimens and 4 antibodies are shown in FIG. 12 (for Clear Cell and Endometrioid) and in FIG. 13 (for Serous and Mucinous). As shown in these drawings, a specific band was detected in a position of respective target molecular weight, and an expression pattern that seems to be tissue-specific was observed similarly to the result obtained by two-dimensional electrophoresis. Each band was quantified based on the band of β-actin (Beta actin) which was a loading control detected from the same sample. For checking the expression pattern for each tissue-type, the significance level (P value) was calculated for each pattern in a similar manner as in Example 1, and a lowermost P value in 14 patterns was obtained respectively in:

Annexin-A4 CM+ ($P<0.0001$),
Maspin precursor M+ ($P<0.0001$),
Cellular retinoic acid-binding protein 2 S+ ($P<0.0001$), and
Phosphoserine aminotransferase C+ ($P<0.0001$). Further, the quantified value in Western blotting was put on the same scale as that of the quantified value in two-dimensional electrophoresis, and plotted in the form of triangle in FIGS. 7 to 10 (previously described). The correlation coefficient of two quantified values in each sample of each protein was $r=0.5$ or more and was significant at a level of $P<0.001$, respectively. This supports the identification result and the expression amount ratio of proteins in Example 1.

As a result of using a result of Western blotting, only the expression pattern of Annexin-A4 was determined as CM+, and a result different from the expression pattern C+ determined in Example 1 was obtained. This is attributed to the fact that the one detected as plural spots, e.g., by post-translational modification in two-dimensional electrophoresis and the like, is detected without distinguished in Western blotting.

That is, when a marker protein is detected by a method other than the two-dimensional electrophoresis method allowing distinction between presence and absence of post-translational modification, it can be detected without distinction of post-translational modification. In such a case, it is particularly preferred to conduct a preliminary experiment prior to detection. For example, when a Western blotting method is selected as a method different from the two-dimensional electrophoresis method (hereinafter, ditto with the case where a method other than the Western blotting method is selected), the requirements if detection results significantly correlate with each other between both detection methods of the two-dimensional electrophoresis method and the Western blotting method, and if significance as a marker is kept ($P<0.01$) are examined in the preliminary experiment. Here, the expression "detection results significantly correlate with each other between both detection methods" indicates the condition that the Spearman's correlation function $\rho$ is a positive number and significant at a level of 5% ($P<0.05$).

When the above requirements are not satisfied both in the case where the Western blotting method is used and in the case where the two-dimensional electrophoresis method is used, it may be determined that selecting the Western blotting method is not reasonable. On the other hand, when it is determined that an expression pattern that is different from that obtained using the two-dimensional electrophoresis method is more significant in the case where the Western blotting method is used, a use method different from an original expression pattern may be employed only in the selected Western blotting method.

For example, Annexin-A4 is one of the examples in which an expression pattern different from that obtained by using the two-dimensional electrophoresis method can be determined as more significant when the Western blotting method is used. Therefore, Annexin-A4 may be used as a CM+ marker when the Western blotting method is used.

Besides the above, within the range grasped in the present invention from the result of Example 1, Alpha crystalline B chain, Phosphoserine Aminotransferase and Purine Nucleoside Phosphorylase were observed in two or more spots in two-dimensional electrophoresis. Among these, for Phosphoserine Aminotransferase, it was determined that the same expression pattern C+ is shown also in Western blotting. When Phosphoserine Aminotransferase is used as a marker, since the expression tendency coincides between tissues irrespectively of presence or absence of post-translational modification in the result of Example 1, it seems to be usable as a C+ marker regardless of whether or not the quantification method allowing distinction between presence and absence of post-translational modification as a quantification method to use. As for Annexin-A4, when a quantification method not allowing distinction between presence and absence of post-translational modification from the result of Example 3 is used, it may be used as a marker of CM+. As for Alpha crystalline B chain and Purine Nucleoside Phosphorylase, a preliminary experiment is separately conducted in the detection method to use and validation according to the aforementioned criteria is examined, thereby each of them may be used as a marker in the detection method.

Next, for using this quantified value according to Western blotting as a marker, an ROC curve was plotted based on whether it is the same or not with the expression pattern, and the value at which sensitivity is 100% was set as a threshold of the marker. For example, in the case of Annexin-A4, since the expression pattern is CM+, the lowest quantified value in samples of Clear Cell and Mucinous is a threshold. As a result, each sample may be evaluated as a combination of whether quantified values of four proteins are not less than the threshold (+) or less than the threshold (−).

Results of tissue-type classification based on expression levels of four proteins using the Western blotting method are shown in FIG. 14. In FIG. 14, frequencies at which specific combinations occur are summarized. This result demonstrates that tissue-types of 38 specimens (95%) among used 40 specimens are correctly classified by this method. For example, taking 13 specimens of Clear Cell as one example among the specimens used in the present example, all of these showed a combination of expression levels ANXA4(+), MASPIN(−), CRABP2(−) and PSAT1(+), and no specimen of other tissue-type had this combination. Therefore, when this combination is detected by the Western blotting method from a specimen whose tissue-type is unknown, it may be predicted that the specimen has high possibility of being Clear Cell.

From the above description, it was confirmed that molecular typing of tissue-type is effectively possible by a detection method based on biospecific affinity using antibodies against a small number of proteins.

The Examples described above show concrete embodiments within the scope of the present invention, but the present invention is not limited to these Examples and may be implemented in various embodiments. Therefore, the Examples described above are merely illustrative in every respect, and should not be construed as being restrictive. Further, the changes that fall within the equivalents of the claims are all within the scope of the present invention.

The invention claimed is:

1. A method of classifying ovarian cancer tissue as being of a clear cell tissue-type, comprising:
    subjecting an ovarian cancer tissue sample originated from an individual of interest to a treatment for detecting Annexin A4,
    detecting Annexin A4 protein in ovarian cancer tissue sample,
    comparing the expression of Annexin A4 protein in the ovarian cancer tissue sample to expression of Annexin A4 protein in endometrioid type and mucinous type ovarian cancer tissue samples, and
    identifying the ovarian cancer tissue sample as a clear cell tissue-type when Annexin A4 is upregulated.

* * * * *